US008753821B2

(12) United States Patent
Hyldig-Nielsen et al.

(10) Patent No.: US 8,753,821 B2
(45) Date of Patent: Jun. 17, 2014

(54) **PNA PROBES, MIXTURES, METHODS AND KITS PERTAINING TO THE DETERMINATION OF *MYCOPLASMA* AND RELATED *MOLLICUTES***

(75) Inventors: Jens Hyldig-Nielsen, Moss Beach, CA (US); Susan Rigby, Acton, MA (US); Michael Tanner, Brentwood, CA (US); Ditte Lee, Cambridge, MA (US); Byron Brehm-Stecher, Ames, IA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 13/400,316

(22) Filed: Feb. 20, 2012

(65) Prior Publication Data

US 2012/0295254 A1  Nov. 22, 2012

Related U.S. Application Data

(63) Continuation of application No. 12/421,927, filed on Apr. 10, 2009, now abandoned, which is a continuation of application No. 11/418,387, filed on May 4, 2006, now abandoned.

(60) Provisional application No. 60/678,331, filed on May 6, 2005.

(51) Int. Cl.
*C12Q 1/68* (2006.01)

(52) U.S. Cl.
USPC ........................................................ 435/6.12

(58) Field of Classification Search
None
See application file for complete search history.

(56) References Cited

U.S. PATENT DOCUMENTS

| | | | |
|---|---|---|---|
| 5,985,563 A | 11/1999 | Hyldig-Nielsen et al. | |
| 6,054,278 A | 4/2000 | Dodge et al. | |
| 6,355,421 B1 | 3/2002 | Coull et al. | |
| 6,436,638 B1 | 8/2002 | De et al. | |
| 6,558,902 B1* | 5/2003 | Hillenkamp | 506/6 |
| 6,783,961 B1 | 8/2004 | Edwards et al. | |
| 2002/0123060 A1 | 9/2002 | Boles et al. | |
| 2003/0077808 A1 | 4/2003 | Rosen | |
| 2003/0175727 A1 | 9/2003 | Hyldig-Nielsen et al. | |
| 2004/0005555 A1* | 1/2004 | Rothman et al. | 435/6 |
| 2004/0043379 A1 | 3/2004 | Hashimoto et al. | |
| 2007/0042350 A1 | 2/2007 | Li et al. | |
| 2011/0111393 A1 | 5/2011 | Hyldig-nielsen et al. | |

FOREIGN PATENT DOCUMENTS

| | | |
|---|---|---|
| WO | WO-99/57318 | 11/1999 |
| WO | WO-03/100076 | 12/2003 |
| WO | WO-2005/005658 | 1/2005 |

OTHER PUBLICATIONS

Hopert et al. (1993) In vitro Cell. Dev. Biol. 29A:819-821.*
Svanvik et al. (2000) Analytical Biochemistry vol. 287: pp. 179-182.*
Kuppeveld et al. (1992) Applied and Environmental Microbiol. vol. 58 No. 8 pp. 2606-2615.*
Bascunana, et al, Characterization of the 16S rRNA genes from *Mycoplasma* sp. strain F38 and development of an identification system based on PCR, J. Bacteriol 176 (9), 1994, 2577-2586.

(Continued)

*Primary Examiner* — Suchira Pande

(57) ABSTRACT

This invention is related to PNA probes, probe sets, mixtures, methods and kits pertaining to the determination of *Mycoplasma* and related Mollicutes.

10 Claims, 10 Drawing Sheets

(56) References Cited

OTHER PUBLICATIONS

Brehm-Stecher et al. "A PNA-Based Real Time PCR Assay for Detection of *Mycoplasma* Contaminants" presented at the American Society for Microbiology Conference, Jun. 5-9, 2005.

Buck, et al, Design Strategies and Performance of Custom DNA Sequencing Primers, Biotechniques, vol. 27, Sep. 1999, 528-536.

Dussurget, et al, Rapid, sensitive PCR-based detection of *Mycoplasmas* in simulated samples of animal sera, 1994 Appl. Environ. Microbiol 60:953-959.

Haier, et al, Detection of mycoplasmal infections in blood of patients with rheumatoid arthritis, Rheumatology 1999, 38: 504-509.

Hart, et al, Absence of *Mycoplasma* contamination in the anthrax vaccine. Emerg. Infect. Dis. 2002, 8: 94-96.

Jensen et al, Unexpected cross-reaction with *Fusobacterium necrophorum* in a PCR for detection of *Mycoplasmas*. J. Clin. Microbiol. 1999, 37: 828-829.

Kidder, et al, Assessment of archived paraffin-embedded cervical condyloma tissues for *Mycoplasma*-conserved DNA using sensitive PCR-ELISA. Gynecol. Oncol. 1998, 71: 254-257.

Kong, et al, Species-specific PCR for identification of common contaminant mollicutes in cell culture. Appl. Environ. Microbiol. 2001, 67: 3195-3200.

Paez-Rubio, et al, Applied and Environ Microbiol vol. 71 No. 2, Feb. 2005), p. 804-810.

Persson, et al, Variable surface protein Vmm of *Mycoplasma mycoides* subsp. *Mycoides* small colony type. J. Bacteriol. 2002, 184: 3712-3722.
Razin, et al, Molecular biology and pathogenicity of *Mycoplasmas*. Microbiol. Mol. Biol. Rev. 1998, 62:1094-1156.
Rottem, et al, Beware of *Mycoplasmas*. Trends Biotechnol. 1993, 11: 143-151.
Tang, et al, A polymerase chain reaction based method for detecting *Mycoplasma/Acholeplasma* contaminants in cell culture. J. Microbiol. Methods 2000, 39: 121-126.
Uphoff, et al, Detection of *Mycoplasma* contaminations in cell cultures by PCR analysis. Hum. Cell 1999, 12: 229-236.
Van Kuppeveld, et al., Detection of *Mycoplasma* contamination in cell cultures by a *Mycoplasma* group-specific PCR. Appl. Environ. Microbiol. 1994, 60: 149-152.
Van Kuppeveld, et al., Genus- and species-specific identification of *Mycoplasmas* by 16S rRNA amplification. Appl. Environ. Microbiol. 1992, 58: 2606-2615.
Yoshida, et al., Phylogeny-based rapid identification of *Mycoplasmas* and ureaplasmas from urethritis patients. J. Clin. Microbiol. 2002, 40: 105-110.
06759338.4, "European Search Report dated May, 15, 2009", 8 Pgs.
PCT/US2006/017764, "International Search Report mailed Nov. 30, 2006", 2 Pgs.

* cited by examiner

Experimental Notes:
- Sequence Nos. 1 and 2 used as DNA based primers
- Sequence No. 6 used as a self indicating PNA probe
- This combination of sequences targets *M. arginini,M. hominis,M. orale,M. salivarium,M. arthriditis*
- Non target controls used in this assay: *M. fermentans, A.laidlawii, M. pirum, M. pneumoniae*

Experimental Notes:
- Sequence Nos. 1 and 4 used as DNA based primers
- Sequence No. 8 used as a self indicating PNA probe
- This combination of sequences targets *A. laidlawii*
- Non target controls used in this assay: : *M. pirum, M. arginini, M. fermentans, B. subtilis, P. aeruginosa*

SEQUENCE LISTING

<160> NUMBER OF SEQ ID NOS: 12

<210> SEQ ID NO 1
<211> LENGTH: 25
<212> TYPE: DNA
<213> ORGANISM: Mycoplasma sp.

<400> SEQUENCE: 1
acaggattag ataccctggt agtcc                                      25

<210> SEQ ID NO 2
<211> LENGTH: 23
<212> TYPE: DNA
<213> ORGANISM: Mycoplasma sp.

<400> SEQUENCE: 2
cctttgagtt tcactcttgc gag                                        23

<210> SEQ ID NO 3
<211> LENGTH: 23
<212> TYPE: DNA
<213> ORGANISM: Mycoplasma sp.

<400> SEQUENCE: 3
cctttaagtt ttattcttgc gaa                                        23

<210> SEQ ID NO 4
<211> LENGTH: 26
<212> TYPE: DNA
<213> ORGANISM: Mycoplasma sp.

<400> SEQUENCE: 4
gtcaattcct ttgagtttca tacttg                                     26

<210> SEQ ID NO 5
<211> LENGTH: 24
<212> TYPE: DNA
<213> ORGANISM: Mycoplasma sp.

<400> SEQUENCE: 5
aattccgttt gagtttcatt cttg                                       24

<210> SEQ ID NO 6
<211> LENGTH: 16
<212> TYPE: DNA
<213> ORGANISM: Mycoplasma sp.

<400> SEQUENCE: 6
ctgagtagta tgctcg                                                16

<210> SEQ ID NO 7
<211> LENGTH: 16
<212> TYPE: DNA
<213> ORGANISM: Mycoplasma sp.

```
<400> SEQUENCE: 7
ctgagtagta cgttcg                                                           16

<210> SEQ ID NO 8
<211> LENGTH: 15
<212> TYPE: DNA
<213> ORGANISM: Mycoplasma sp.

<400> SEQUENCE: 8
agtacgtacg caagt                                                            15

<210> SEQ ID NO 9
<211> LENGTH: 17
<212> TYPE: DNA
<213> ORGANISM: Mycoplasma sp.

<400> SEQUENCE: 9
gtagtacatt cgcaaga                                                          17

<210> SEQ ID NO 10
<211> LENGTH: 22
<212> TYPE: DNA
<213> ORGANISM: Mycoplasma sp.

<400> SEQUENCE: 10
catccgcaca ctatctcatc gt                                                    22

<210> SEQ ID NO 11
<211> LENGTH: 23
<212> TYPE: DNA
<213> ORGANISM: Mycoplasma sp.

<400> SEQUENCE: 11
ccacactatc aatgccagaa cgg                                                   23

<210> SEQ ID NO 12
<211> LENGTH: 120
<212> TYPE: DNA
<213> ORGANISM: Mycoplasma sp.

<400> SEQUENCE: 12
tttttttttt tttttttttt catccgcaca ctatctcatc gttatcgttc catcagctcg           60
ttgatcttcc gttctggcat tgatagtgtg gcggttggat ccctatagtg agtcgtatta          120
```

PNA PROBES, MIXTURES, METHODS AND KITS PERTAINING TO THE DETERMINATION OF *MYCOPLASMA* AND RELATED *MOLLICUTES*

CROSS-REFERENCE TO RELATED APPLICATIONS

This application is a continuation of U.S. patent application Ser. No. 12/421,927 filed Apr. 10, 2009 now abandoned, which is a continuation of U.S. patent application Ser. No. 11/418,387 filed May 4, 2006 now abandoned and claims the benefit of U.S. Provisional Patent Application No. 60/678,331 filed May 6, 2005, which disclosures are herein incorporated by reference in their entirety.

The section headings used herein are for organizational purposes only and are not to be construed as limiting the subject matter described in any way.

1. FIELD

This invention is related to the field of detection, analysis and/or quantification of microorganisms such as for the determination of *Mycoplasma* and related Mollicutes.

2. INTRODUCTION

Members of the Class Mollicutes are among the smallest and simplest of the prokaryotes. This Class includes species from the genera *Mycoplasma, Acholeplasma* and *Ureaplasma*, and may be agents of disease and/or present as adventitious contaminants in cell culture, or in certain products and processes. Because of their small size and lack of a rigid cell wall, members of the Class Mollicutes (referred to hereafter simply as "Mollicutes") pass easily through filters intended to remove bacterial contaminants. Because of their small size, these organisms have limited biosynthetic capabilities, making them dependent on external sources for essential nutrients and cofactors. Many species of Mollicutes have therefore evolved to become intracellular parasites.

All species of *Mycoplasma* are considered a risk as potential cell culture contaminants. As contaminants, *Mycoplasma* species have been shown to exert a wide variety of negative effects on cultured cells. For example, *Mycoplasma* species can compete with cultured cells for essential nutrients or can produce toxins that can cause cell death, all of which can impact the quality and productivity of cell cultures. These organisms are therefore of significant concern to the biopharmaceutical industry, which is dependent on continuous cell culture for the production of drugs, vaccines, and other "biologics". Members of the genus *Acholeplasma*, especially *Acholeplasma laidlawii*, are also of substantial concern as an adventitious cell culture, product or process contaminants.

Current culture methods for detection of Mollicutes are limited by the time required for the growth of these fastidious organisms. As a result, detection of Mollicutes using these methods can take 28 days or longer, a timeframe that is not compatible with today's fast pace of pharmaceutical manufacturing and distribution. Access to rapid, simple and relatively inexpensive methods for the detection of Mollicutes would enable the routine testing and proactive quality control of cell cultures, raw materials, equipment, fixtures and the like.

3. DRAWINGS

The skilled artisan will understand that the drawings, described below, are for illustration purposes only. The drawings are not intended to limit the scope of the present teachings in any way.

All literature and similar materials cited in this application, including but not limited to, patents, patent applications, articles, books, treatises, and internet web pages, regardless of the format of such literature and similar materials, are expressly incorporated by reference herein in their entirety for any and all purposes.

4. DEFINITIONS

Figure 1A:
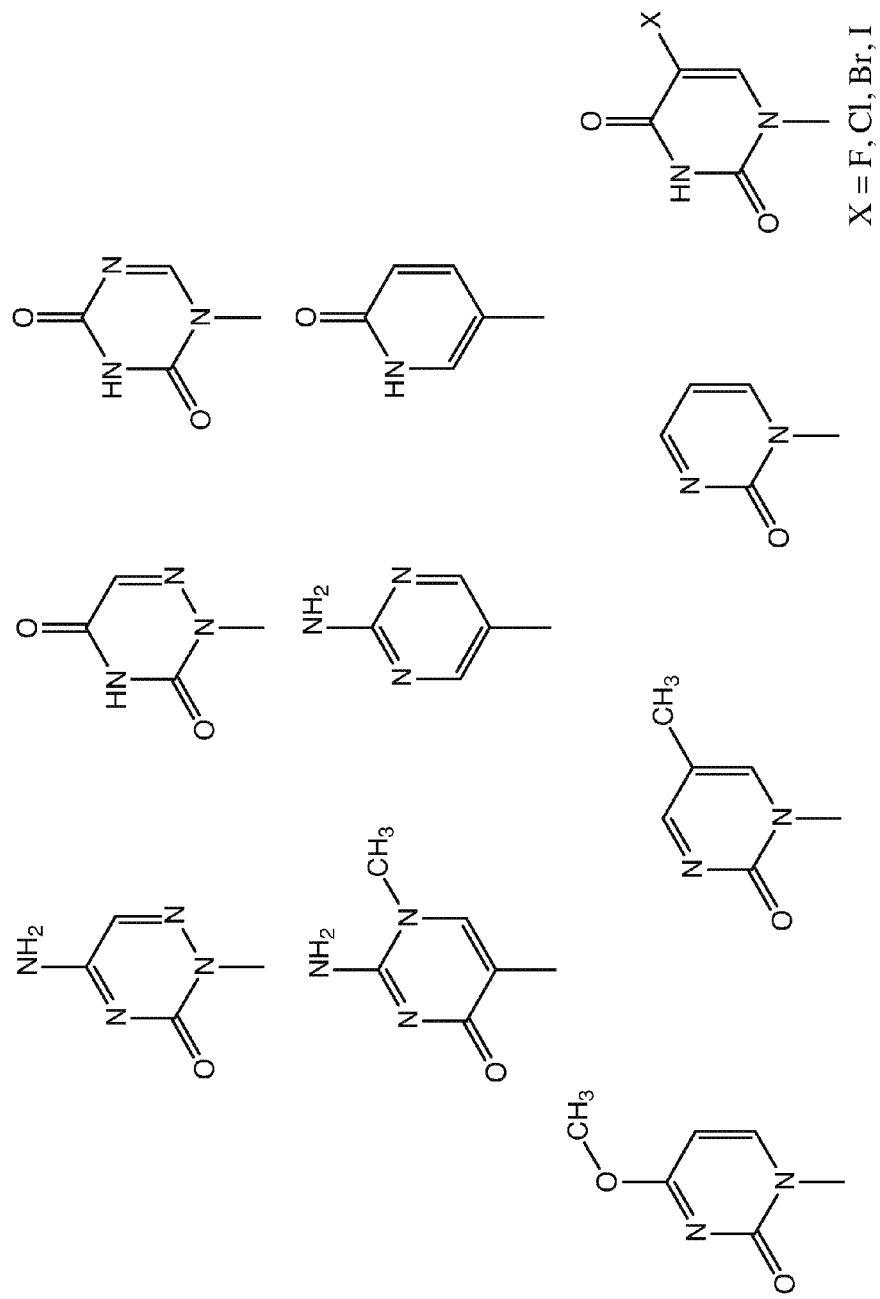
FIGS. 1A and 1B are illustrations of some nucleobases that can be incorporated into the nucleic acid primers and/or PNA probes used in various embodiments of this invention.
Figure 1B:
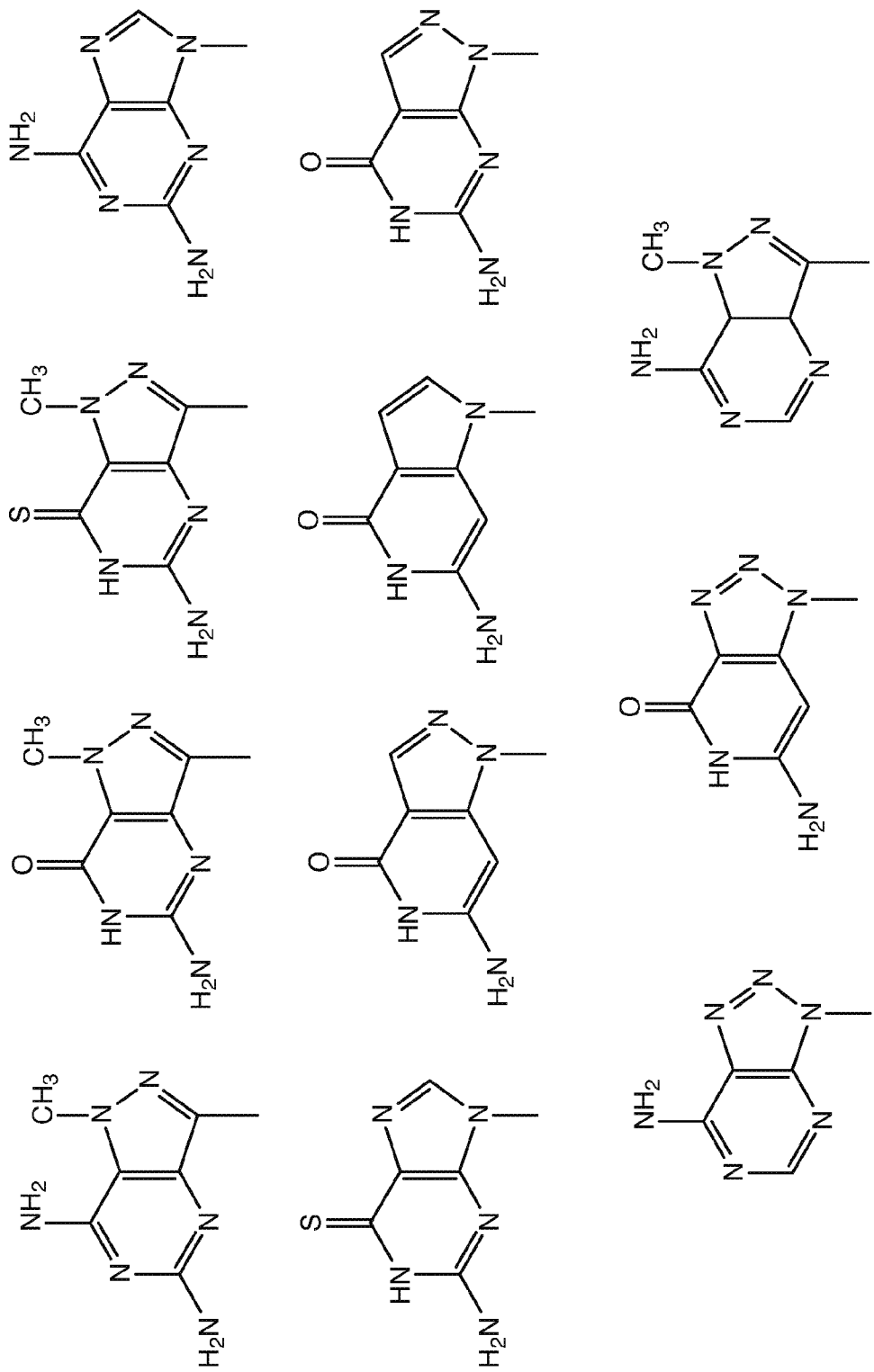

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall control.

a. As used herein, "nucleobase" refers to those naturally occurring and those non-naturally occurring heterocyclic moieties commonly known to those who utilize nucleic acid technology or utilize peptide nucleic acid technology to thereby generate polynucleobase strands that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 1A and 1B (also see U.S. Pat. No. 6,357,163).

b. As used herein, "nucleobase sequence" refers to any segment, or aggregate of two or more segments, of a polynucleobase strand. Non-limiting examples of suitable polynucleobase strands include oligodeoxynucleotides (e.g. DNA), oligoribonucleotides (e.g. RNA), peptide nucleic acids (PNA), PNA chimeras, nucleic acid analogs and/or nucleic acid mimics.

c. As used herein, the phrase "nucleobase containing subunit" refers to a subunit of a polynucleobase strand that comprises a nucleobase. For oligonucleotides, the nucleobase containing subunit is a nucleotide. For peptides and proteins, the subunits are amino acids. With reference to oligonucleotides and peptides, those of skill in the art will appreciate the form of a subunit associated with other species of polynucleobase strands.

d. As used herein, "target sequence" refers to a nucleobase sequence of a polynucleobase strand sought to be determined. The target sequence can be a subsequence of the rRNA of a Mollicute. The target sequence can be a subsequence of the rDNA of a Mollicute. The target sequence can also be a subsequence of cDNA of the rRNA of a Mollicute. The target sequence can be a subsequence of the genomic DNA of a Mollicute. The target sequence can be a subsequence of the mRNA of a Mollicute. The target sequence can be a subsequence of a polynucleobase strand (including a polynucleobase strand of an amplicon) produced from a nucleic acid amplification reaction. Non-limiting examples of nucleic acid amplification reactions include: Polymerase Chain Reaction (PCR), Ligase Chain Reaction (LCR), Strand Displacement Amplification (SDA), Transcription-Mediated Amplification (TMA), Rolling Circle Amplification (RCA)), Cycling Probe Technology (CPT), Loop-Mediated Isothermal Amplification (LAMP), Linear Target Isothermal Multimerization and Amplification (LIMA), and Q-beta replicase.

e. As used herein, "polynucleobase strand" refers to a complete single polymer strand comprising nucleobase containing subunits.

f. As used herein, "nucleic acid" refers to a nucleobase sequence-containing polymer, or polynucleobase strand, having a backbone formed from nucleotides, or analogs thereof. Preferred nucleic acids are DNA, RNA, L-DNA, locked nucleic acids (LNA). For the avoidance of any doubt, PNA is a nucleic acid mimic and not a nucleic acid or nucleic acid analog. PNA is not a nucleic acid since it is not formed from nucleotides.

g. As used herein, "peptide nucleic acid" or "PNA" refers to any polynucleobase strand or segment of a polynucleobase strand comprising two or more PNA subunits, including, but not limited to, any polynucleobase strand or segment of a polynucleobase strand referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 and 6,357,163.

The term "peptide nucleic acid" or "PNA" shall also apply to any polynucleobase strand or segment of a polynucleobase strand comprising two or more subunits of those nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diderichsen, U., *Bioorganic & Medicinal Chemistry Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:5 55-560 (1997); Howarth et al., *J. Org. Chem.* 62: 5441-5450 (1997); Altmann, K-H et al., *Bioorganic & Medicinal Chemistry Letters*, 7: 1119-1122 (1997); Diederichsen, U., *Bioorganic & Med. Chem. Lett.,* 8: 165-168 (1998); Diederichsen et al., *Angew. Chem. Int. Ed.,* 37: 302-305 (1998); Cantin et al., *Tett. Lett.,* 38: 4211-4214 (1997); Ciapetti et al., *Tetrahedron,* 53: 1167-1176 (1997); Lagriffoule et al., *Chem. Eur. J.,* 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000.

In some embodiments, a "peptide nucleic acid" or "PNA" is a polynucleobase strand or segment of a polynucleobase strand comprising two or more covalently linked subunits of the formula:

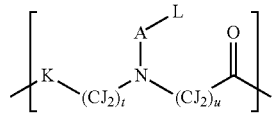

wherein, each J is the same or different and is selected from the group consisting of: H, $R^1$, $OR^1$, $SR^1$, $NHR^1$, $NR^1_2$, F, Cl, Br and I. Each K is the same or different and is selected from the group consisting of: O, S, NH and $NR^1$. Each $R^1$ is the same or different and is an alkyl group having one to five carbon atoms that can optionally contain a heteroatom or a substituted or unsubstituted aryl group. Each A is selected from the group consisting of: a single bond, a group of the formula; —$(CJ_2)_s$- and a group of the formula; —$(CJ_2)_s$C(O)—, wherein, J is defined above and each s is a whole number from one to five. Each t is 1 or 2 and each u is 1 or 2. Each L is the same or different and is independently selected from: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine), N8-(7-deaza-8-aza-adenine), other naturally occurring nucleobase analogs and other non-naturally occurring nucleobases (e.g. FIGS. 1A and 1B).

In some embodiments, a PNA subunit can be a naturally occurring or non-naturally occurring nucleobase attached to the N-α-glycyl nitrogen of the N-[2-(aminoethyl)]glycine backbone through a methylene carbonyl linkage; this currently being the most commonly used form of a peptide nucleic acid subunit.

h. As used herein, the terms "label", "reporter moiety" or "detectable moiety" are interchangeable and refer to moieties that can be attached to polynucleobase strand or antibody, or otherwise be used in a reporter system, to thereby render the polynucleobase strand or antibody detectable by an instrument or method. For example, a label can be any moiety that: (i) provides a detectable signal; (ii) interacts with a second label to modify the detectable signal provided by the first or second label; or (iii) confers a capture function (e.g. hydrophobic affinity, antibody/antigen, ionic complexation).

i. As used herein, "sequence specifically" refers to hybridization by base pairing through hydrogen bonding. Non-limiting examples of standard base pairing include adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza- 8-aza-guanine); thymine or uracil base pairing with any of: 2-aminopurine, N9-(2-amino-6-chloropurine) or N9-(2,6-diaminopurine); and N8-(7-deaza-8-aza-adenine), being a universal base, base pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine) or N9-(7-deaza-8-aza-guanine) (See: Seela et al., *Nucl. Acids, Res.:* 28(17): 3224-3232 (2000)).

j. As used herein, the term "chimera" or "chimeric oligomer" refers to a polynucleobase strand comprising two or more linked subunits that are selected from different classes of subunits. For example, a PNA/DNA chimera can comprise at least one PNA subunits linked to at least one 2'-deoxyribonucleic acid subunit (For exemplary methods and compositions related to PNA/DNA chimera preparation See: WO96/40709). Exemplary component subunits of the chimera can be selected from the group consisting of PNA subunits, naturally occurring amino acid subunits, DNA subunits, RNA subunits and subunits of analogues or mimics of nucleic acids.

k. As used herein, the term "linked polymer" refers to a polynucleobase strand comprising two or more polymer segments which are linked by a linker. The polymer segments that can be linked to form the linked polymer can be selected from the group consisting of an oligodeoxynucleotide, an oligoribonucleotide, a peptide, a polyamide, a peptide nucleic acid (PNA) and a chimera.

l. As used herein, the terms "mollicute" or "Mollicutes" refer to one or more species of the genera *Mycoplasma, Acholeplasma* or *Ureaplasma*.

m. As used herein "solid support" or "solid carrier" refers to any solid phase material upon which a polynucleobase strand can be synthesized, attached, ligated or otherwise immobilized. Solid support encompasses terms such as "resin", "solid phase", "surface" and "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection means including scanning by laser illumination and confocal or deflective light gathering.

n. As used herein, "support bound" refers to immobilization on, or to, a solid support. It is understood that immobilization can occur by any means, including for example; by covalent attachment, by electrostatic immobilization, by attachment through a ligand/ligand interaction, by contact or by depositing on the surface.

5. DESCRIPTION

I. General:

It is to be understood that the discussion set forth below in this "General" section can pertain to some, or to all of, the various embodiments of the invention described herein. The use of "or" means "and/or" unless stated otherwise. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of".

PNA Synthesis:

Methods for the chemical assembly of PNAs are well-known (See for example: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470. As a general reference for PNA synthesis methodology please see: Nielsen et al., *Peptide Nucleic Acids; Protocols and Applications*, Horizon Scientific Press, Norfolk England (1999).

Chemicals and instrumentation for the support bound automated chemical assembly of peptide nucleic acids are available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that can be condensed with the next synthon to be added to the growing polymer. Because standard peptide chemistry is utilized, natural and non-natural amino acids can be routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide. The orientation of hybridization is not a limitation however, since PNA oligomers are also known to bind in parallel orientation to both nucleic acids and other PNA oligomers.

PNA Labeling:

Non-limiting methods for labeling PNA oligomers are described in U.S. Pat. Nos. 6,110,676, 6,355,421, 6,361,942 and 6,485,901 or are otherwise well known in the art of PNA synthesis. Other non-limiting examples for labeling PNA oligomers are also discussed in Nielsen et al., *Peptide Nucleic Acids; Protocols and Applications*, Horizon Scientific Press, Norfolk England (1999). PNA oligomers and oligonucleotides can also be labeled with proteins (e.g. enzymes) and peptides as described in U.S. Pat. No. 6,197,513. Thus, a variety of labeled PNA oligomers can be prepared or purchased from commercial vendors.

Nucleic Acid Synthesis and Modification

Nucleic acid oligomer (oligonucleotide and oligoribonucleotide) synthesis has become routine. For a detailed description of nucleic acid synthesis please see Gait, M. J., *Oligonucleotide Synthesis: a Practical Approach. IRL Press, Oxford England*. Those of ordinary skill in the art will recognize that both labeled and unlabeled oligonucleotides (DNA, RNA and synthetic analogues thereof) are readily available. They can be synthesized using commercially available instrumentation and reagents or they can be purchased from commercial vendors of custom manufactured oligonucleotides.

Chimera Synthesis And Modification:

PNA chimeras are a combination of a nucleic acid and peptide nucleic acid subunits. A suitable reference for the synthesis, labeling and modification of PNA chimeras can be found in U.S. Pat. No. 6,063,569. Moreover, the methods described above for PNA synthesis and labeling often can be used to modify the PNA portion of a PNA chimera. Additionally, well-known methods for the synthesis and labeling of nucleic acids can often be used to modify the nucleic acid portion of a PNA chimera. Hence, the synthesis, labeling and modification of PNA chimeras can utilize methods known to those of skill in the art as well as those described, or made reference to, above.

Labels:

Non-limiting examples of detectable moieties (labels) that can be used to label polynucleobase strands (e.g. PNA probes) or antibodies used in embodiments of this invention can include a dextran conjugate, a branched nucleic acid detection system, a chromophore, a fluorophore, a spin label, a radioisotope, an enzyme, a hapten, an acridinium ester or a chemiluminescent compound. Other suitable labeling reagents and preferred methods of attachment would be recognized by those of ordinary skill in the art of PNA, peptide or nucleic acid synthesis.

Non-limiting examples of haptens include 5(6)-carboxyfluorescein, 2,4-dinitrophenyl, digoxigenin, and biotin.

Non-limiting examples of fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Non-limiting examples of enzymes include polymerases (e.g. Taq polymerase, Klenow DNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

Energy Transfer

In some embodiments, polynucleobase strands can be labeled with an energy transfer set. For energy transfer to be useful in determining hybridization, there should be an energy transfer set comprising at least one energy transfer donor and at least one energy transfer acceptor moiety. Often, the energy transfer set will include a single donor moiety and a single acceptor moiety, but this is not a limitation. An energy transfer set can contain more than one donor moiety and/or more than one acceptor moiety. The donor and acceptor moieties operate such that one or more acceptor moieties accept energy transferred from the one or more donor moieties or otherwise quench the signal from the donor moiety or moieties. Thus, in some embodiments, both the donor moiety(ies) and acceptor moiety(ies) are fluorophores. Though the previously listed fluorophores (with suitable spectral properties) might also operate as energy transfer acceptors, the acceptor moiety can also be a non-fluorescent quencher moiety such as 4-((−4-(dimethylamino)phenyl)azo) benzoic acid (dabcyl). The labels of the energy transfer set can be linked at the termini of the polynucleobase strand or linked at a site within the polynucleobase strand. For example, each of two labels of an energy transfer set can be linked at the distal-most termini of the polynucleobase strand.

Transfer of energy between donor and acceptor moieties can occur through any energy transfer process, such as through the collision of the closely associated moieties of an energy transfer set(s) or through a non-radiative process such as fluorescence resonance energy transfer (FRET). For FRET to occur, transfer of energy between donor and acceptor moieties of a energy transfer set requires that the moieties be close in space and that the emission spectrum of a donor(s) have substantial overlap with the absorption spectrum of the acceptor(s) (See: Yaron et al. *Analytical Biochemistry*, 95: 228-235 (1979) and particularly page 232, col. 1 through page 234, col. 1). Alternatively, collision mediated (radiationless) energy transfer can occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228-235 (1979) and particularly page 229, col. 1 through page 232, col. 1). This process is referred to as intramolecular collision since it is believed that quenching is caused by the direct contact of the donor and acceptor moieties (See: Yaron et al.). Energy transfer can also occur through processes for which the mechanism of action has yet to be described. It is to be understood that any reference to energy transfer in the instant application encompasses all of these mechanistically distinct phenomena. It is also to be understood that energy transfer can occur though more than one energy transfer process simultaneously and that the change in detectable signal can be a measure of the simultaneous and/or sequential activity of two or more energy transfer processes. Accordingly, the mechanism of energy transfer is not a limitation to the embodiments of this invention.

Detecting Energy Transfer in a Self-Indicating Polynucleobase Strand:

When labeled with an energy transfer set, we refer to a polynucleobase strand as being self-indicating. Non-limiting examples of self-indicating nucleic acid oligomers have been described in U.S. Pat. Nos. 6,103,476, 6,150,097 and 6,365, 729. Non-limiting examples of self-indicating PNA oligomers have been described in U.S. Pat. Nos. 6,355,421, 6,485, 901, 6,528,267 and 6,649,349. In some cases, the self-indicating oligomers can be used as primers in a nucleic acid amplification reaction (e.g. U.S. Pat. Nos. 5,866,366, 6,090, 552, 6,117,635 and 6,365,729).

Hybrid formation between a self-indicating oligomer and a target sequence can be monitored by measuring at least one physical property of at least one member of the energy transfer set that is detectably different when the hybridization complex is formed as compared with when the oligomer exists in a non-hybridized state. We refer to this phenomenon as the self-indicating property of the polynucleobase strand. This change in detectable signal results from the change in efficiency of energy transfer between donor and acceptor moieties caused by hybridization of the oligomer to the target sequence.

Figure 2A:
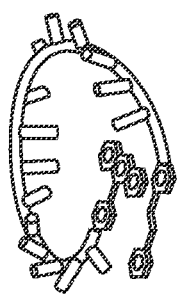
FIG. 2 is an illustration of a self-indicating PNA probe in its unhybridized (a) and hybridized (b) state. In its unhybridized state (a) the fluorescence is substantially quenched and in the hybridized state (b) there is a substantial increase in detectable fluorescence.
Figure 2B:
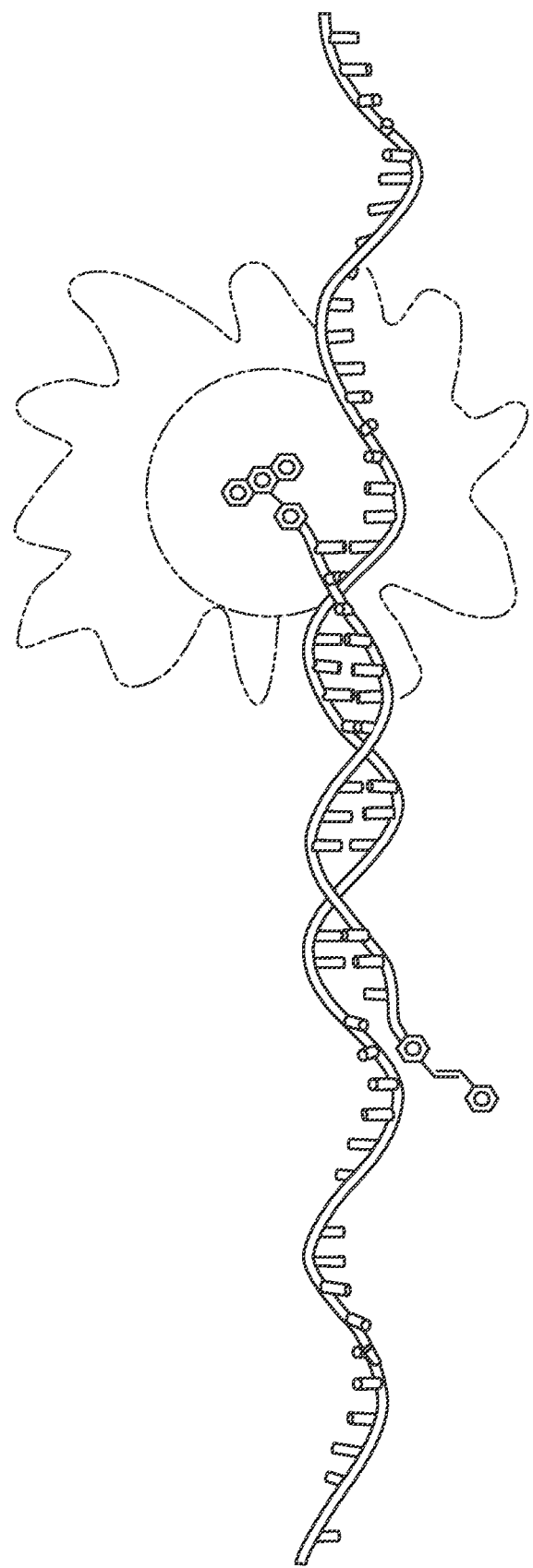

For example, the means of detection can involve measuring fluorescence of a donor or acceptor fluorophore of an energy transfer set. In some embodiments, the energy transfer set can comprise at least one donor fluorophore and at least one acceptor (fluorescent or non-fluorescent) quencher such that the measure of fluorescence of the donor fluorophore can be used to detect, identify or quantitate hybridization of the oligomer to the target sequence. For example, there can be a measurable increase in fluorescence of the donor fluorophore upon the hybridization of the oligomer to a target sequence (See: FIG. 2).

In some embodiments, the energy transfer set can comprise at least one donor fluorophore and at least one acceptor fluorophore such that the measure of fluorescence of either, or both, of at least one donor moiety or one acceptor moiety can be used to can be used to detect, identify and/or quantify hybridization of the self-indicating oligomer to the target sequence.

Self-indicating PNA oligomers can be used in in-situ hybridization assays. Self-indicating PNA oligomers are also useful for the analysis of nucleic acid amplification reactions either in real-time or at the end point.

Detectable and Independently Detectable Moieties/Multiplex Analysis:

A multiplex hybridization assay can be performed in accordance with embodiments of this invention. In a multiplex assay, numerous conditions of interest can be simultaneously examined. Multiplex analysis relies on the ability to sort sample components or the data associated therewith, during or after the assay is completed. In various embodiments of the invention, one or more distinct independently detectable moieties can be used to label two or more different probes used in an assay. The ability to differentiate between and/or quantitate each of the independently detectable moieties provides the means to multiplex a hybridization assay because the data that correlates with the hybridization of each of the distinctly (independently) labeled probe to a particular target sequence can be correlated with the presence, absence and/or quantity of each organism (e.g. a mollicute) sought to be detected in the sample. Consequently, the multiplex assays of this invention can be used to simultaneously detect the presence, absence and/or quantity of two or more different organisms (e.g. a mollicute) in the same sample and in the same assay. For example, a multiplex assay can utilize two or more PNA probes, each being labeled with an independently detectable fluorophore, or a set of independently detectable fluorophores Spacer/Linker Moieties:

Generally, spacers are used to minimize the adverse effects that bulky labeling reagents might have on hybridization properties of probes. Linkers typically induce flexibility and randomness into the polynucleobase strand or otherwise link two or more nucleobase sequences of a polynucleobase strand. Preferred spacer/linker moieties for the polynucleobase strands described herein can comprise one or more aminoalkyl carboxylic acids (e.g. aminocaproic acid), the side chain of an amino acid (e.g. the side chain of lysine or ornithine), natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties can also incidentally or intentionally be constructed to improve the water solubility of the polynucleobase strand (For example see: Gildea et al., *Tett. Lett.* 39: 7255-7258 (1998) and U.S. Pat. Nos. 6,326,479 and 6,770,442).

For example, a spacer/linker moiety can comprise one or more linked compounds having the formula: $-Y-(O_m-(CW_2)_n)_o-Z-$. The group Y can be selected from the group consisting of: a single bond, $-(CW_2)_p-$, $-C(O)(CW_2)_p-$, $-C(S)(CW_2)_p-$ and $-S(O_2)(CW_2)_p$. The group Z can have the formula $NH$, $NR^2$, S or O. Each W can be independently H, $R^2$, $-OR^2$, F, Cl, Br or I; wherein, each $R^2$ can be independently selected from the group consisting of: $-CX_3$, $-CX_2CX_3$, $-CX_2CX_2CX_3$, $-CX_2CX(CX_3)_2$, and $-C(CX_3)_3$. Each X can be independently H, F, Cl, Br or I. Each m can be independently 0 or 1. Each n, o and p can be independently integers from 0 to 10.

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination can often be found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay can be experimentally determined by examination of each stringency factor until the desired degree of discrimination is achieved.

Suitable Hybridization Conditions:

Generally, the more closely related the background causing nucleic acid contaminants are to the target sequence, the more careful stringency must be controlled. Blocking probes can also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods, kits and compositions described herein. Suitable hybridization conditions can be applied to both the hybridization of probes to target sequences as well as to the hybridization of primers to primer sites such as in a real-time PCR reaction. Suitable in-situ hybridization conditions comprise conditions suitable for performing an in-situ hybridization procedure. Thus, suitable hybridization or suitable in-situ hybridization conditions are well-known in the biological arts and specific conditions for achieving the desired level of discrimination can be achieved using the disclosure provided herein, with or without additional routine experimentation.

Blocking Probes:

Blocking probes are nucleic acid or non-nucleic acid probes (e.g. PNA probes) that can be used to suppress the binding of the probing nucleobase sequence of the probing polymer to a non-target sequence. PNA oligomers can be blocking probes (See: Coull et al., U.S. Pat. No. 6,110,676). Typically, blocking probes are closely related to the probing nucleobase sequence and preferably they comprise a point mutation as compared with the probing nucleobase sequence. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with various embodiments of this invention to thereby suppress the binding of the PNA probe to a non-target sequence that might be present and interfere with the performance of the assay. Blocking probes can be applied to in single point mutation discrimination.

Probing Nucleobase Sequence:

The probing nucleobase sequence of a polynucleobase strand is the specific sequence recognition portion of the construct. For example, the probing nucleobase sequence of a PNA probe is a sequence of nucleobases designed to sequence specifically hybridize to a target sequence wherein the presence, absence and/or amount of target sequence can be used to determine the presence, absence and/or quantity of an organism (e.g. a mollicute) in a sample. Thus, with due consideration of the requirements of a PNA probe for the assay format chosen, the length of the probing nucleobase sequence of a probe will generally be chosen such that a stable complex is formed between the PNA probe and the target sequence under suitable hybridization conditions or suitable in-situ hybridization conditions.

Probe Complexes:

In some embodiments, two probes taken together can be designed to hybridize to the target sequence whereby the nucleobase sequence of each probe comprises half or approximately half of the probing nucleobase sequence required for hybridization to the complete target sequence of the organism sought to be detected in the assay. As a non-limiting example, the probing nucleobase sequences of the two probes might be designed as described in U.S. Pat. No. 6,027,893, entitled: "Method of identifying a nucleic acid using triple helix formation of adjacently annealed probes" by H. Orum et al., herein incorporated by reference. Using this methodology, the probes that hybridize to the target sequence may or may not be labeled. However, it is the probe complex formed by the annealing of the adjacent probes that is detected. Similar compositions comprised solely of PNA probes have been described in U.S. Pat. No. 6,287,772.

Linked Polymers:

In some embodiments, linked polymers can be used as probes. As defined previously a linked polymer refers to a polynucleobase strand comprising two or more polymer segments that are linked by a linker. Accordingly, in some embodiments, the PNA probe can be designed to comprise two nucleobase sequences whereby each of the two nucleobase sequences comprises half or approximately half of the probing nucleobase sequence required for hybridization to the complete target sequence of the organism sought to be detected in the assay. Where more than two polymer segments are used, two or more of the linked polymer segments can be combined so that the aggregate nucleobase sequence of the various segments comprises the probing nucleobase sequence required for hybridization to the target sequence of the organism sought to be detected in the assay.

Primers:

In various embodiments, polynucleobase strands can be used as primers in nucleic acid amplification reactions. The primers can be oligonucleotides. The primers can be PNA/DNA chimeras. In some embodiments, the primers can be labeled. In some embodiments, the primers can be unlabeled. The primers can be used in nucleic acid amplification reactions such as in a PCR amplification reaction.

Asymmetric & Asynchronous PCR:

In some embodiments, asymmetric or asynchronous PCR can be used in an assay.

Asymmetric PCR has been described by Gyllensten et al. in U.S. Pat. No. 5,066,584 and has been used in combination with self-indicating probes in U.S. Pat. Nos. 6,485,901 and 6,649,349. Asynchronous PCR has been described by Chen et al. in WO01/94638. In both cases, the amplification reaction produces more of one polynucleobase strand of the double stranded template than it does of the other strand wherein the polynucleobase strand produced in excess comprises the target sequence.

Internal Positive Control:

In some embodiments, an Internal Positive Control (IPC) may be included in a amplification assay assay. The IPC may consists of an independent set of primers, probe and target DNA. The IPC can be included to confirm that amplification has occurred in the assay. By confirming that amplication occurred in the reaction, it is possible to rule out amplification failure in cases where a negative result is obtained. Amplification of the IPC may be performed in a separate tube or well or together with one or more of the probes and primers detecting *Mycoplasma* and related Mollicutes. The target DNA may either be cloned into a plasmid or be an oligonucleotide. Internal positive controls are commercially available.

II. Various Embodiments of the Invention a. PNA Probes:

In some embodiments, this invention is directed to one or more PNA probes. The PNA probe or probes can be selected for determining *Mycoplasma* and related Mollicutes (such as *Acholeplasma* and/or *Ureaplasma*) in a sample. Determination can include detecting, identifying and/or quantifying *Mycoplasma, Acholeplasma* and/or *Ureaplasma* species in a sample. The PNA probe or probes can be used for the analysis of nucleic acid, whether or not it is present within an organism of interest. Accordingly, this invention can be used for the analysis of organisms (e.g. in-situ analysis) as well as for the analysis of nucleic acid extracted from, or derived from, an organism of interest (e.g. PCR analysis). Thus, the source of the target sequence is not a limitation.

TABLE 1

Probe & Primer Sequences

| SEQ. ID. No. | Probe or Primer | Nucleobase Sequence |
|---|---|---|
| 1 | Nucleic Acid Primer | ACA-GGA-TTA-GAT-ACC-CTG-GTA-GTC-C |
| 2 | Nucleic Acid Primer | CCT-TTG-AGT-TTC-ACT-CTT-GCG-AG |
| 3 | Nucleic Acid Primer | CCT-TTA-AGT-TTT-ATT-CTT-GCG-AA |
| 4 | Nucleic Acid Primer | GTC-AAT-TCC-TTT-GAG-TTT-CAT-ACT-TG |
| 5 | Nucleic Acid Primer | AAT-TCC-GTT-TGA-GTT-TCA-TTC-TTG |
| 6 | PNA Probe | CTG-AGT-AGT-ATG-CTC-G |

TABLE 1-continued

Probe & Primer Sequences

| SEQ. ID. No. | Probe or Primer | Nucleobase Sequence |
|---|---|---|
| 7 | PNA Probe | CTG-AGT-AGT-ACG-TTC-G |
| 8 | PNA Probe | AGT-ACG-TAC-GCA-AGT |
| 9 | PNA Probe | GTA-GTA-CAT-TCG-CAA-GA |

Notes:
1) Nucleobase sequences are illustrated 5'-3' for Nucleic Acids and N-terminus to C-terminus for PNA.
2) A database search was conducted in order to determine the similarity of the Nucleic Acid Primer sequences to existing PCR primer sequences published for the detection of Mycoplasma and related species of the Class Mollicutes. Using the "align two sequences" function available from the National Center for Biotechnology Information (http://www.ncbi.nlm.nih.gov/blast/bl2seq/bl2.html), SEQ ID. Nos. 1-9 were compared with a set of over 50 published Mycoplasma-targeted primers (Dussurget and Roulland-Dussoix, 1994; Kong et al., 2001; Tang et al., 2000; Uphoff and Drexler, 1999; van Kuppeveld, et al., 1994). SEQ. ID. Nos. 2, 3, 5 and 6-9 did not overlap with any of the primers screened, while SEQ. ID. Nos. 1 and 4 showed some homology to known primers.

Generally, this invention can be useful for the determination of Mollicutes. The PNA probes can comprise a probing nucleobase sequences that is useful for the specific determination of one or more genus of species of Mollicute. The probing nucleobase sequence of various PNA probes suitable for detecting target sequences in one or more Mollicutes are listed as SEQ ID Nos. 6-9 of Table 1. Thus, in some embodiments, the PNA probe can comprise SEQ. ID. NO: 6, SEQ. ID. NO: 7, SEQ. ID. NO: 8, SEQ. ID. NO: 9, the complement to SEQ. ID. NO: 6, the complement to SEQ. ID. NO: 7, the complement to SEQ. ID. NO: 8 or the complement to SEQ. ID. NO: 9. Taken in combination with the primers identified as SEQ ID Nos. 1-5, one or more PCR amplification reactions can be performed to determine the organisms listed in Table 2. Table 2 identifies greater than 100 species of organisms belonging to the Class Mollicutes.

In some embodiments, the PNA probe or probes can have a length of 12-20 nucleobase containing subunits. In some embodiments, the PNA probe or probes can have a length of 13-18 nucleobase containing subunits. In some embodiments, the PNA probe or probes can have a length of 15-17 nucleobase containing subunits. In some embodiments, the probing nucleobase sequence of the PNA probe or probes can be chosen to have the exact nucleobase sequence listed in Table 1. Accordingly, in some embodiments, the probing nucleobase sequence of the PNA probe is SEQ. ID. NO: 6, SEQ. ID. NO: 7, SEQ. ID. NO: 8, SEQ. ID. NO: 9, the complement to SEQ. ID. NO: 6, the complement to SEQ. ID. NO: 7, the complement to SEQ. ID. NO: 8 or the complement to SEQ. ID. NO: 9. Complements of the probing nucleobase sequences listed as SEQ ID Nos. 6-9 of Table 1 are potentially useful in the manufacture of suitable PNA probes since it is possible to prepare or amplify copies of the target sequence wherein the copies are complements of the target sequence and thus, will bind to the complement of the nucleobase sequences listed in Table 1.

TABLE 2

Species of *Mycoplasma*, *Acholeplasma* and *Ureaplasma*

*Mycoplasma* species

M. adleri
M. agalactiae
M. agassizii
M. alconis
M. alkalescens
M. alligatoris
M. alvi
M. anatis
M. anseris
M. arginini
M. arthritidis
M. auris
M. bovigenitalium
M. bovirhinis
M. bovis
M. bovoculi
M. buccale
M. californicum
M. canadense
M. canis
M. capricolum
M. caviae
M. citelli
M. cloacale
M. collies
M. columbinasale
M. columbinum
M. columborale
M. conjunctivae
M. corogypsi
M. cottewii
M. cricetuli
M. crocodyli
M. cynos
M. dispar
M. edwardii
M. elephantis
M. equigenitalium
M. equithinis
M. fastidiosum
M. faucium
M. felifaucium
M. felis
M. fermentans
M. flocculare
M. gallinaceum
M. gallinarum
M. gallisepticum
M. gateae
M. genitalium
M. gypis
M. hominis
M. hyopneumoniae
M. hyorhinis
M. imitans
M. indiense

TABLE 2-continued

Species of Mycoplasma, Acholeplasma and Ureaplasma

M. iners
M. iowae
M. lacerti
M. lagogenitalium
M. leocaptivus
M. leopharyngis
M. lipofaciens
M. maculosum
M. meleagridis
M. microti
M. moatsii
M. mobile
M. molare
M. monodon
M. muris
M. mustelae
M. mycoides
M. neurolyticum
M. opalescens
M. orale
M. ovipneumoniae
M. oxoniensis
M. penetrans
M. phocae
M. phocicerebrale
M. phocirhinis
M. pirum
M. pneumoniae
M. primatum
M. pullorum
M. pulmonis
M. putrefaciens
M. salivarium
M. simbae
M. spermatophilum
M. spumans
M. sturni
M. sturnidae
M. sualvi
M. subdolum
M. synoviae
M. testudinis
M. verecundum
M. volis
M. yeatsii
M. zalophus

Acholeplasma and Ureaplasma species

| | |
|---|---|
| A. axanthum | U. canigenitalium |
| A. laidlawii | U. cati |
| A. oculi | U. diversum |
| A. polakii | U. felinum |
| | U. gallorale |
| | U. urealyticum |

A PNA probe can have a probing nucleobase sequence that is complementary to the target sequence. Alternatively, a substantially complementary probing nucleobase sequence can be used since it has been demonstrated that greater sequence discrimination can be obtained when utilizing probes wherein there exists one or more point mutations (base mismatch) between the probe and the target sequence (See: Guo et al., *Nature Biotechnology* 15:331-335 (1997)).

This invention contemplates that variations in the probing nucleobase sequences listed in Table 1 can provide PNA probes that are suitable for the specific detection of the organisms listed in Table 2. Common variations include, deletions, insertions and frame shifts. Variations of the probing nucleobase sequences within the parameters described herein are considered to be embodiments of this invention.

The PNA probe or probes can comprise only a probing nucleobase sequence (as previously described herein) or can comprise additional moieties. Non-limiting examples of additional moieties include detectable moieties (labels), linkers, spacers, natural or non-natural amino acids, peptides, enzymes and/or other subunits of PNA, DNA or RNA. Additional moieties can be functional or non-functional in an assay. Generally however, additional moieties will be selected to be functional within the design of the assay in which the PNA probe can be used. For example, the PNA probe or probes can be labeled with one or more detectable moieties or labeled with two or more independently detectable moieties. The independently detectable moieties can be independently detectable fluorophores. Whether detectable or independently detectable, the PNA probe or probes can be self-indicating. Non-limiting examples of labels have been previously described herein.

The PNA probes can be used in in-situ hybridization (ISH) and fluorescence in-situ hybridization (FISH) assays (e.g. See U.S. Pat. Nos. 6,280,946, 6,649,349, 6,656,687 and 6,664,045). The PNA probes can be used in nucleic acid amplification reactions (e.g. See U.S. Pat. Nos. 6,355,421, 6,361,942, 6,441,152, 6,485,901 and 6,649,349).

Excess probe is sometimes removed from an assay so that the detectable moiety of specifically hybridized probes can be detected above the background signal that results from still present but unhybridized probe. However, because certain types of self-indicating probes can generate little or no detectable background, they can be used to eliminate the requirement that excess probe be completely removed (washed away) from the sample.

Unlabeled Non-Nucleic Acid Probes:

The probes of this invention need not be labeled with a detectable moiety to be operable. When using PNA probes it is possible to detect the PNA probe/target sequence complex formed by hybridization of the probing nucleobase sequence of the probe to the target sequence. For example, a PNA/nucleic acid complex formed by the hybridization of a PNA probing nucleobase sequence to the target sequence can be detected using an antibody that specifically interacts with the complex under antibody binding conditions. Suitable antibodies to PNA/nucleic acid complexes and methods for their preparation and use are, for example, described in U.S. Pat. No. 5,612,458.

The antibody/PNA/nucleic acid complex formed by interaction of the α-PNA/nucleic acid antibody with the PNA/nucleic acid complex can be detected by several methods. For example, the α-PNA/nucleic acid antibody could be labeled with a detectable moiety. Suitable detectable moieties have been previously described herein. Thus, the presence, absence and/or quantity of the detectable moiety can be correlated with the presence, absence and/or quantity of the antibody/PNA/nucleic acid complex and the one or more Mollicutes to be identified. Alternatively, the antibody/PNA/nucleic acid complex can be detected using a secondary antibody that is labeled with a detectable moiety. Typically the secondary antibody specifically binds to the α-PNA/nucleic acid antibody under antibody binding conditions. Thus, the presence, absence and/or quantity of the detectable moiety can be correlated with the presence, absence and/or quantity of the antibody/antibody/PNA/nucleic acid complex and the one or more Mollicutes to be identified. As used herein, the term antibody includes antibody fragments that specifically bind to other antibodies or other antibody fragments.

Immobilization of Probes to a Surface:

In some embodiments, the PNA probe or probes can be used in solution. In some embodiments, the PNA probe or probes can be immobilized on supports. Accordingly, one or more of the PNA probes can optionally be immobilized to a surface for the detection of the target sequence of a target organism of interest.

PNA probes can be immobilized to the surface using the well-known process of UV-crosslinking. A PNA probe can be synthesized on the surface in a manner suitable for deprotection but not cleavage from the synthesis support (See: Weiler, J. et al, Hybridization based DNA screening on peptide nucleic acid (PNA) oligomer arrays, Nucl. Acids Res., 25, 14.2792-2799 (July 1997)). In still another embodiment, PNA probes can be covalently linked to a surface by the reaction of a suitable functional group on the probe with a functional group of the surface (See: U.S. Pat. No. 6,475,721).

Methods for the chemical attachment of PNA probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the probe. Because native PNA possesses an amino terminus, a PNA will not necessarily require modification to thereby immobilize it to a surface (See: U.S. Pat. No. 6,475,721).

Conditions suitable for the immobilization of a PNA probe to a surface will generally be similar to those conditions suitable for the labeling of the polymer. The immobilization reaction is essentially the equivalent of labeling whereby the label is substituted with the surface to which the polymer is to be linked.

Numerous types of surfaces derivatized with amino groups, carboxylic acid groups, isocyantes, isothiocyanates and malimide groups are commercially available. Non-limiting examples of suitable surfaces include membranes, chips (e.g. silicone chips), glass, controlled pore glass, polystyrene particles (beads), silica and gold nanoparticles.

Arrays of PNA Probes:

Arrays are surfaces to which two or more probes have been immobilized each at a specified position. Arrays of PNA probes are described, for example in, U.S. Pat. No. 6,475,721 as well as in Weiler, J. et al, Hybridization based DNA screening on peptide nucleic acid (PNA) oligomer arrays, Nucl. Acids Res., 25, 14.2792-2799 (July 1997). The probing nucleobase sequence of the immobilized probes can be judiciously chosen to interrogate a sample that can contain nucleic acid from one or more target organisms. Because the location and composition of each immobilized probe is known, arrays can be useful for the simultaneous detection, identification and/or quantification of nucleic acid from two or more target organisms (e.g. one or more Mollicutes) that can be present in the sample. Moreover, arrays of PNA probes can be regenerated by stripping away any of the hybridized nucleic acid after each assay, thereby providing a means to repetitively analyze numerous samples using the same array. Thus, arrays of PNA probes or PNA probe sets can be useful for repetitive screening of samples for target organisms of interest. The arrays can comprise at least one PNA probe or more than on PNA probe. PNA probes comprising the probing nucleobase sequences identified in Table 1 can be suitable for determining one or more Mollicutes listed in Table 2.

b. PNA Probe Sets:

In some embodiments, this invention is also directed to probe sets suitable for detecting, identifying and/or quantifying one or more Mollicutes in a sample. The general and preferred characteristics of PNA probes suitable for the determination of one or more Mollicutes have been previously described herein. Exemplary probing nucleobase sequences suitable for use in such probes are listed as SEQ ID Nos. 6-9 of Table 1. One or more of such PNA probes can be combined with one or more other probes to form a probe set.

Accordingly, in some embodiments, at least one PNA probe of the set can comprise SEQ. ID. NO: 6, SEQ. ID. NO: 7, SEQ. ID. NO: 8, SEQ. ID. NO: 9, the complement to SEQ. ID. NO: 6, the complement to SEQ. ID. NO: 7, the complement to SEQ. ID. NO: 8 or the complement to SEQ. ID. NO: 9 as the probing nucleobase sequence. In some embodiments, the probe set can comprise a PNA probe comprising SEQ. ID. NO: 6 as the probing nucleobase sequence, a PNA probe comprising SEQ. ID. NO: 7 as the probing nucleobase sequence, a PNA probe comprising SEQ. ID. NO: 8 as the probing nucleobase sequence and/or a PNA probe comprising SEQ. ID. NO: 9 as the probing nucleobase sequence. In some embodiments, the PNA probe set can comprise a PNA probe of SEQ. ID. NO: 6, a PNA probe of SEQ. ID. NO: 7, a PNA probe of SEQ. ID. NO: 8 and/or a PNA probe of SEQ. ID. NO: 9.

The grouping of PNA probes within sets characterized for specific determination of one or more Mollicutes can be a very powerful embodiment of this invention. Probe sets can comprise at least one PNA probe but need not comprise only PNA probes. For example, probe sets can comprise mixtures of PNA probes and nucleic acid probes and/or nucleic acid primers, provided however that a set comprises at least one PNA probe as described herein. PNA probes useful for determining one or more Mollicutes can be combined with probes for other organisms. Probe sets can be combined with primers and/or other reagents selected to perform an assay such as an in-situ hybridization assay or a PCR assay. In some embodiments, some of the probes of the set can be blocking probes composed of PNA or nucleic acid.

Table 1 lists two or more probing nucleobase sequences suitable for the determination of one or more Mollicutes. Where alternative probing nucleobase sequences exist, a probe set comprising two or more PNA probes can be used to thereby increase the detectable signal in the assay. Two or more PNA probes can also be combined in a set to thereby increase the number of species that can be determined in a single assay.

In some embodiments, the probe set can comprise two or more independently detectable PNA probes wherein each independently detectable probe is suitable for determining a different Mollicute, or set of Mollicutes, in a sample. Such an assay could be a multiplex assay wherein each of two or more genera of Mollicutes, or species of Mollicutes, is independently determined if present in the sample. In some multiplex assays, suitable independently detectable probes can be used for determining each of the different species to be identified, detected and/or quantified.

c. Mixtures:

In some embodiments, this invention is also directed to mixtures suitable for detecting, identifying and/or quantifying one or more Mollicutes in a sample. The mixtures can comprise one or more PNA probes as described herein. The general and preferred characteristics of PNA probes suitable for the determination of Mollicutes have been previously described herein. Exemplary probing nucleobase sequences suitable for use in such probes are listed as SEQ ID Nos. 6-9 of Table 1.

Combining probes into a mixture for the specific determination of Mollicutes can be a very powerful embodiment of this invention. Such mixtures can comprise at least one PNA probe but need not comprise only PNA probes. Such mixtures can combine PNA probes, nucleic acid probes, and/or nucleic acid primers. Such mixtures can combine PNA probes useful for determining one or more Mollicutes with probes for the determination of other organisms. Mixtures combining PNA probes with primers and/or other reagents can be selected to perform an assay such as an in-situ hybridization assay or a PCR assay. In some embodiments, probes of the mixture can include blocking probes composed of either PNA or nucleic acid.

In some embodiments, the components combined to form the mixture can be selected to perform an assay. For example, the components of the mixture can be selected to perform a nucleic acid amplification reaction as part of an assay used to detect, identify and/or quantify one or more Mollicutes in a sample. Such a mixture can comprise at least two nucleic acid primers, of 15-30 nucleotides in length, each capable of hybridizing to a primer site in the nucleic acid of a Mollicute and at least one PNA probe, of 12-20 nucleobase containing subunits, capable of hybridizing to the target sequence in the nucleic acid of a Mollicute.

For example, the at least two nucleic acid primers can each comprise, or consist of, SEQ ID. NO: 1, SEQ ID. NO: 2, SEQ ID. NO: 3, SEQ ID. NO: 4 or SEQ ID. NO: 5. Similarly, the probing nucleobase sequence of the one or more PNA probes can each comprise, or consist of: SEQ. ID. NO: 6, SEQ. ID. NO: 7, SEQ. ID. NO: 8, SEQ. ID. NO: 9, the complement to SEQ. ID. NO: 6, the complement to SEQ. ID. NO: 7, the complement to SEQ. ID. NO: 8 or the complement to SEQ. ID. NO: 9. One such mixture can comprise: a) a primer of SEQ ID NO: 1; a primer of SEQ ID NO: 2; a primer of SEQ ID NO: 3; a primer of SEQ ID NO: 4; and/or a primer of SEQ ID NO: 5; as well as, b) a PNA probe consisting of SEQ. ID. NO: 6 as the probing nucleobase sequence; a PNA probe consisting of SEQ. ID. NO: 7 as the probing nucleobase sequence; a PNA probe consisting of SEQ. ID. NO: 8 as the probing nucleobase sequence; and/or a PNA probe consisting of SEQ. ID. NO: 9 as the probing nucleobase sequence.

In some embodiments, the mixture can further comprise other reagents selected to perform a PCR amplification reaction. In some embodiments, the mixture can further comprise an internal positive control. Such reagents and controls are commercially available or are otherwise well known to those of ordinary skill in the art.

In some embodiments, the components of the mixture are selected to perform an in-situ hybridization assay. In-situ analysis using PNA probes is well known (See: U.S. Pat. Nos. 6,280,946, 6,649,349, 6,656,687 and 6,664,045). Accordingly, with no more than routine experimentation and the information disclosed herein, it is possible to select components of a mixture suitable for determining one or more Mollicutes.

In some embodiments, the components of the mixture can be selected to perform a multiplex assay, whereby more than one organism is determined. In some cases the multiplex assay can be designed to determine two or more species of Mollicute. In some cases the multiplex assay can be designed to determine more than two species of *Mycoplasma*.

The amount of each component of a mixture will be selected based upon the requirements of the assay. Accordingly, the amounts of probes and primers can be dictated by the specific design of the assay. Because much is known about using PNA probes and primers in various species of assays, no more than routine experimentation combined with the disclosure set forth herein will be involved in determining the amounts the components needed to formulate mixtures suitable for performing such assays.

d. Methods:

In some embodiments, this invention is also directed to methods suitable for determining one or more Mollicutes in a sample. The general and preferred characteristics of PNA probes suitable for the determination of Mollicutes have been previously described herein. Exemplary probing nucleobase sequences are listed as SEQ ID Nos. 6-9 of Table 1.

In some embodiments, the method can comprise: a) contacting a sample with one or more PNA probes of 12-20 nucleobase containing subunits, wherein each of the one or more PNA probes comprises a probing nucleobase sequence comprising, or consisting of: SEQ. ID. NO: 6, SEQ. ID. NO: 7, SEQ. ID. NO: 8 or SEQ. ID. NO: 9; and b) determining hybridization of the probing nucleobase sequence of the PNA probe or probes to at least one target sequence in the sample, under suitable hybridization conditions or suitable in-situ hybridization conditions, and correlating the result with the presence, absence and/or quantity of one or more Mollicutes in the sample. This correlation is possible by direct or indirect determination of the probe/target sequence complex.

In some embodiments, the method is performed as an in-situ hybridization assay. Organisms to be analyzed by in-situ methods can be prepared for analysis by various methods. The cells can be fixed on slides and visualized with a film, camera, slide scanner or microscope. Alternatively, the cells can be fixed and then analyzed in a flow cytometer. Slide scanners and flow cytometers are particularly useful for rapidly quantifying the number of target organisms present in a sample of interest.

Nucleic acid from organisms can also be analyzed. Typically for these analysis the nucleic acid of the organism is collected, often through harvesting of the nucleic acid after the cells of the organism have been lysed.

Where the nucleic acid is harvested, a nucleic acid amplification reaction can be performed. Thus, in some embodiments, the method can further comprise: c) contacting the sample with at least two nucleic acid primers, of 15-30 nucleotides in length, and other reagents selected to perform a PCR amplification reaction; and d) performing a PCR amplification reaction to thereby produce one or more amplicons comprising the target sequence or target sequences. In some embodiments, the nucleic acid primers can each comprise, or consist of, SEQ ID. NO: 1, SEQ ID. NO: 2, SEQ ID. NO: 3, SEQ ID. NO: 4 or SEQ ID. NO: 5. In some embodiments, the PCR assay is an end-point PCR assay or a real-time PCR assay. In some embodiments, the one or more PNA probes are self-indicating (e.g. Example 1).

e. Kits:

In some embodiments, this invention is directed to kits suitable for performing an assay that determines one or more Mollicutes in a sample. The general and preferred characteristics of PNA probes suitable for the detection, identification and/or quantitation of one or more Mollicutes have been previously described herein.

The kits of this invention can comprise one or more PNA probes and other reagents or compositions that are selected to perform an assay or otherwise simplify the performance of an assay. The kits can, for example, comprise buffers and/or other reagents selected for performing a PNA-ISH or PNA-FISH assay. In other embodiments, the buffers and/or other reagents can be selected for performing a nucleic acid amplification reaction such as a PCR reaction. Those of skill in the art will appreciate what types of reagents are typically found in kits used to perform PNA-ISH, PNA-FISH assays or PCR assays.

f. Exemplary Applications for Using Embodiments of the Invention:

The PNA probes, probe sets, mixtures, methods and kits described herein have been demonstrated to be useful for determining one or more Mollicutes. By determining we mean establishing the presence, absence and/or quantity of one or more Mollicutes in a sample. Moreover, the assays described herein can be performed in a rapid manner (as little as 35 minutes in some embodiments; e.g. FIG. 6). The assays can be sensitive, reliable and capable, in a single assay, of the detection and/or enumeration of the organisms listed in Table 2.

Whether support bound or in solution, the PNA probes, probe sets, mixtures, methods and/or kits described herein can be used for the rapid, sensitive and reliable detection of one or more Mollicutes in cell culture of mammalian, insect or plant origin, in finished pharmaceutical products, vaccines or other cell culture-derived biologics, or the raw materials used for their production in personal care products, in dairy products or bottled water, or for the analysis of environmental samples. These can be particularly useful for the analysis of raw materials, equipment, products or processes used to manufacture or store food, water, pharmaceutical products, personal care products, dairy products or for the analysis of environmental samples. Whether support bound or in solution, the PNA probes, probe sets, mixtures, methods and/or kits described herein can be useful for the determination of one or more Mollicutes in clinical or veterinary samples and environments. Non-limiting examples of clinical samples include: sputum, laryngeal swabs, gastric lavage, bronchial washings, biopsies, aspirates, expectorates, body fluids (e.g. spinal, pleural, pericardial, synovial, blood, pus, amniotic, and urine), bone marrow and tissue sections. Suitable PNA probes, probe sets, mixtures, methods and kits can also be particularly useful for the analysis of clinical specimens, equipment, fixtures or products used to treat humans or animals.

6. EXAMPLES

Aspects of the present teachings can be further understood in light of the following examples, which should not be construed as limiting the scope of the present teachings in any way.

All PNA oligomers were prepared using conventional synthesis and purification procedures. All nucleic acid primers were purchased from commercial sources.

Example 1

Detection of Mycoplasma and Related Genera

Although many polymerase chain reaction assays have been devised for the detection of Mycoplasma species and related genera of Mollicutes (Dussurget, et al., 1994; Haier et al., 1999; Jensen et al., 1999; Kidder et al., 1993; Tang et al., 2000; van Kuppeveld et al, 1992; van Kuppeveld et al., 1994), the difficulty in identifying primers that selectively amplify sequences belonging to this large and phylogenetically diverse group of organisms is reflected in the fact that none of these primer sets have been shown to be entirely specific for their intended targets (Kong et al., 2001). The combined use of DNA primers and PNA probes described here for detection of Mycoplasma and related genera is more specific than these previous assays because it contains two layers of specificity. The first layer of specificity lies in the combination of the five DNA primers described here (SEQ ID Nos. 1-5), which were selected to encompass the sequence diversity of this broad group of target organisms. Under the conditions used in the assay described in this Example, these primers were expected to generate amplicons for a number of Mycoplasma species and related genera of Mollicutes, such Acholeplasma and Ureaplasma species.

TABLE 3

List Of Probes & Primers

| Type | Based On | Composition |
|---|---|---|
| DNA primer | SEQ ID No. 1 | HO-ACA-GGA-TTA-GAT-ACC-CTG-GTA-GTC-C-OH |
| DNA primer | SEQ ID No. 2 | HO-CCT-TTG-AGT-TTC-ACT-CTT-GCG-AG-OH |
| DNA primer | SEQ ID No. 3 | HO-CCT-TTA-AGT-TTT-ATT-CTT-GCG-AA-OH |
| DNA primer | SEQ ID No. 4 | HO-GTC-AAT-TCC-TTT-GAG-TTT-CAT-ACT-TG-OH |
| DNA primer | SEQ ID No. 5 | HO-AAT-TCC-GTT-TGA-GTT-TCA-TTC-TTG-OH |
| PNA probe | SEQ ID No. 6 | Dye1-glu-CTG-AGT-AGT-ATG-CTC-G-lys-lys-Dabcyl-NH$_2$ |
| PNA probe | SEQ ID No. 7 | Dye1-glu-CTG-AGT-AGT-ACG-TTC-G-lys-lys-Dabcyl-NH$_2$ |
| PNA probe | SEQ ID No. 8 | Dye1-glu-AGT-ACG-TAC-GCA-AGT-lys-lys-Dabcyl-NH$_2$ |
| PNA probe | SEQ ID No. 9 | Dye1-glu-GTA-GTA-CAT-TCG-CAA-GA-lys-lys-Dabcyl-NH$_2$ |

Notes:
1) glu = glutamic acid; lys = lysine;
2) Nucleobase sequences are illustrated 5'-3' for nucleic acid primers and N-terminus to C-terminus for PNA probes; NH$_2$ indicates that the PNA terminates in an amide group;
3) There is a partial overlap of nucleobase sequence between of some of the primers and some of the probes. Such overlaps are illustrated in Bold text.

Although these primers were designed to avoid amplification of DNA from most closely-related genera of non-target bacteria such as Bacillus, Lactobacillus, Staphylococcus, Streptococcus and Clostridium, it was possible that unexpected cross reactions with other non-target bacteria could occur (Kong et al., 2001; Jensen et al., 1999). The second layer of specificity lies in the use of the four PNA probes described here (Sequences 6-9). Sequence-specific hybridization of these PNA probes was used to report the presence of the four amplicons expected from the Mycoplasma and other Mollicutes targeted by the assay. With these two layers of specificity designed into the assay, amplicons arising from unexpected primer cross-reactions with genomic DNA belonging to non-target organisms or artifacts and side reactions such as primer-dimers formation, did not confound interpretation of the assay results.

Key to Table 3:

Primer Sequences:
- SEQ ID No. 1=broadly reactive forward primer
- SEQ ID No. 2=reverse primer targeting *Mycoplasma arginini, Mycoplasma salivarium, Mycoplasma orale, Mycoplasma arthriditis, Mycoplasma hominis* and related species.
- SEQ ID No. 3=reverse primer targeting *Mycoplasma fermentans* and related species.
- SEQ ID No. 4=reverse primer targeting *Acholeplasma laidlawii* and related species.
- SEQ ID No. 5=reverse primer *Mycoplasma pirum, Mycoplasma pneumoniae, M. genitalium* and related species.

Probe Sequences:
- SEQ ID No. 6=self-indicating PNA probe for the detection of an amplicon generated using combination of SEQ ID No. 1 (forward primer) and SEQ ID No. 2 (reverse primer).
- SEQ ID No. 7=self-indicating PNA probe for detection of amplicon generated using combination of SEQ ID No. 1 (forward primer) and SEQ ID No. 3 (reverse primer).
- SEQ ID No. 8=self-indicating PNA probe for detection of amplicon generated using combination of SEQ ID No. 1 (forward primer) and SEQ ID No. 4 (reverse primer).
- SEQ ID No. 9=self-indicating PNA probe for detection of amplicon generated using SEQ ID No. 1 (forward primer) and SEQ ID No. 5 (reverse primer).

Assay Description:

This assay comprised four PNA probes, one forward PCR primer, and four reverse PCR primers. This probe set was selected to identify nearly all known species of *Mycoplasma*, including the eight "problem" species reported to cause 95% of cell line contamination. This probe set also allows identification of *Acholeplasma* laidlawii, also of significant concern as a cell culture contaminant. Additional target organisms that can be determined using this assay are listed in Table 2. This assay did not target the *Spiroplasma, Entomoplasma, Mesoplasma* (Mollicutes) as well as the non-Mollicute genus *Lactobacillus*.

PCR Conditions:

For real-time PCR reactions, the following conditions were used: To a PCR tube, 40 µL of PCR Mix and 10 µL of *Mycoplasma* or *Acholeplasma* genomic DNA (American Type Culture Collection, Manassas, Va.) or appropriate mixtures thereof, were added. The PCR Mix contained: 1×Buffer A (Applied Biosystems, Foster City, Calif.), 3.0 mM MgCl$_2$, 0.25 mM of each of the four dNTPs (deoxynucleotide triphosphates), 500 nM of PNA probe(s), 100 nM forward primer, 1000 nM of reverse primer(s), 2 units of AmpliTaq™ Gold polymerase (Applied Biosystems, Foster City, Calif.). PCR cycling conditions were carried out in the ABI PRISM 7000 Sequence Detection System using the following cycle protocol:
Preheat: 95° C. for 10 min.
50 cycles of:
 95° C. for 15 sec.
 60° C. for 1 min.

For rapid endpoint PCR reactions, the following conditions were used: To a PCR tube, 20 µL of PCR Mix and 5 µL of a mixture of *Mycoplasma arginini* and *Bacillus subtilis* genomic DNA (American Type Culture Collection, Manassas, Va.) were added. The final concentration of each DNA added was 140 fg. The PCR Mix contained a final concentration of: 1×KOD Hot Start DNA polymerase buffer (Novagen, Madison, Wis.), 2.0 mM MgCl$_2$, 0.25 mM of each of the four dNTPs (deoxynucleotide triphosphates), 500 nM of PNA probe (SEQ. ID NO. 6), 100 nM forward primer (SEQ. ID NO. 1), 1000 nM of reverse primer (SEQ. ID NO. 2), 1 unit of KOD Hot Start DNA polymerase (Novagen, Madison, Wis.) and 1× (50 nM) ROX internal standard dye. PCR cycling conditions were carried out on an ABI 9800 Fast PCR System using the following cycle protocol:
50 cycles of:
 95° C. for 2 sec.
 60° C. for 5 sec.

After completion of PCR, the Fast PCR System plate was transferred to an ABI Prism 7700 Sequence Detection System for collection of spectra and data quantitation. Fluorescence was also easily visualized using an ultraviolet transilluminator.

Internal Positive Control:

The following is a description of the components of the internal positive control used in the PCR assay:

```
PNA Probe:
Vic-Glu-CTC-GTT-GAT-CTT-CCG-Lys-Lys(Dabcyl)

For. Primer:
                                       SEQ ID NO. 10
CAT-CCG-CAC-ACT-ATC-TCA-TCG-T Rev. Primer:
                                       SEQ ID NO. 11
CCA-CAC-TAT-CAA-TGC-CAG-AAC-GG
```

Partial Sequence of the Plasmid—SEQ ID NO. 12

TTT-TTT-TTT-TTT-TTT-TTT-<u>TTC-ATC-CGC-ACA-CTA-TCT-CAT-CGT</u>-TAT-CGT-TCC-ATC-AGC-TCG-TTG-ATC-TTC-CGT-TCT-GGC-ATT-GAT-AGT-GTG-GCG-GTT-GGA-TCC-CTA-TAG-TGA-GTC-GTA-TTA

Bold text illustrates the primer sites in the IPC and underlined text illustrates the binding site of the PNA probe. Vic labeled PNA probes are commercially available from Applied Biosystems.

Figure 3A:
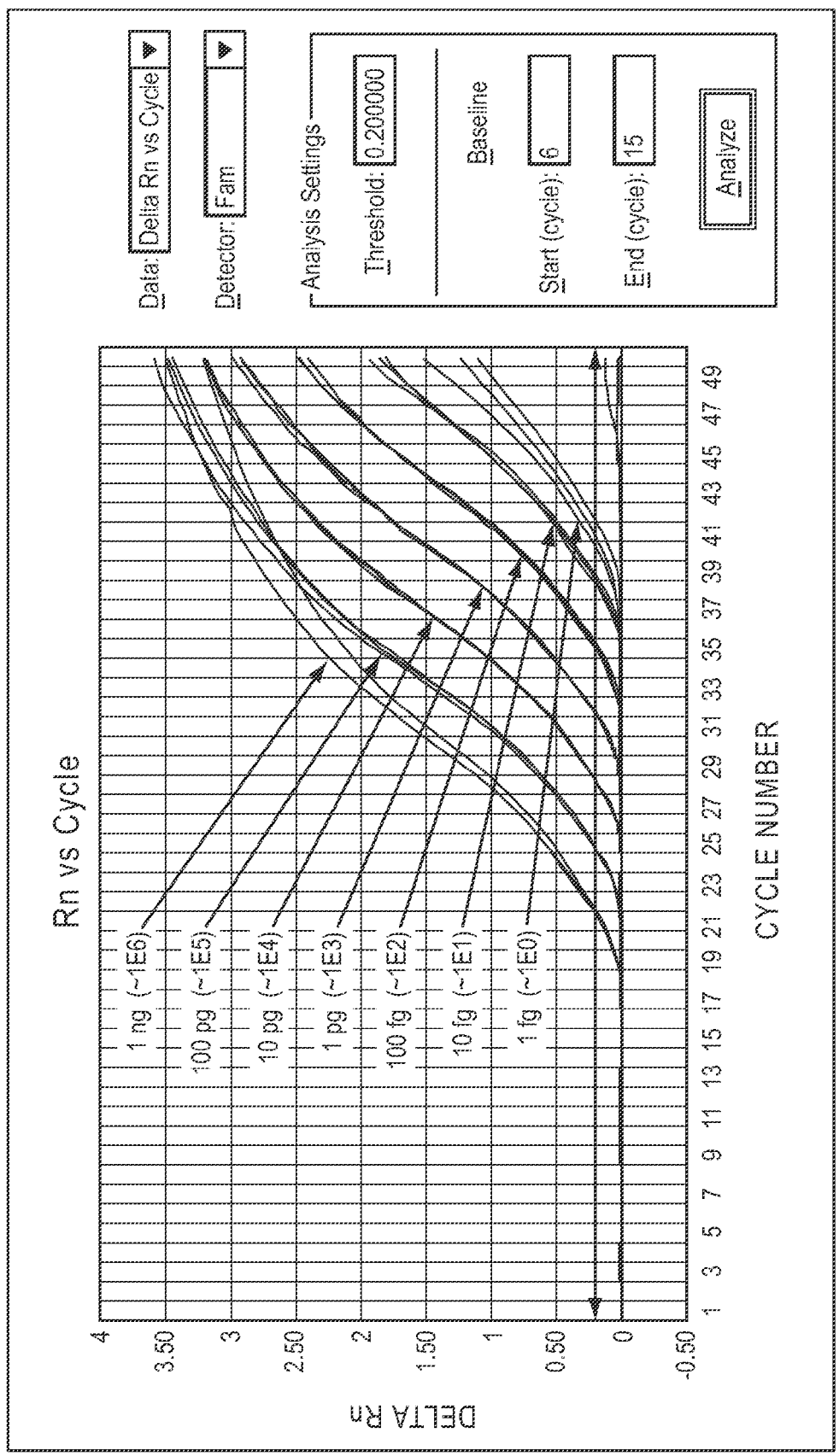
FIG. 3A is data output from an ABI 7700 for real-time sensitivity and specificity testing of an assay for Mollicutes using at least two nucleic acid primers and at least one PNA probe described herein.
Figure 3B:
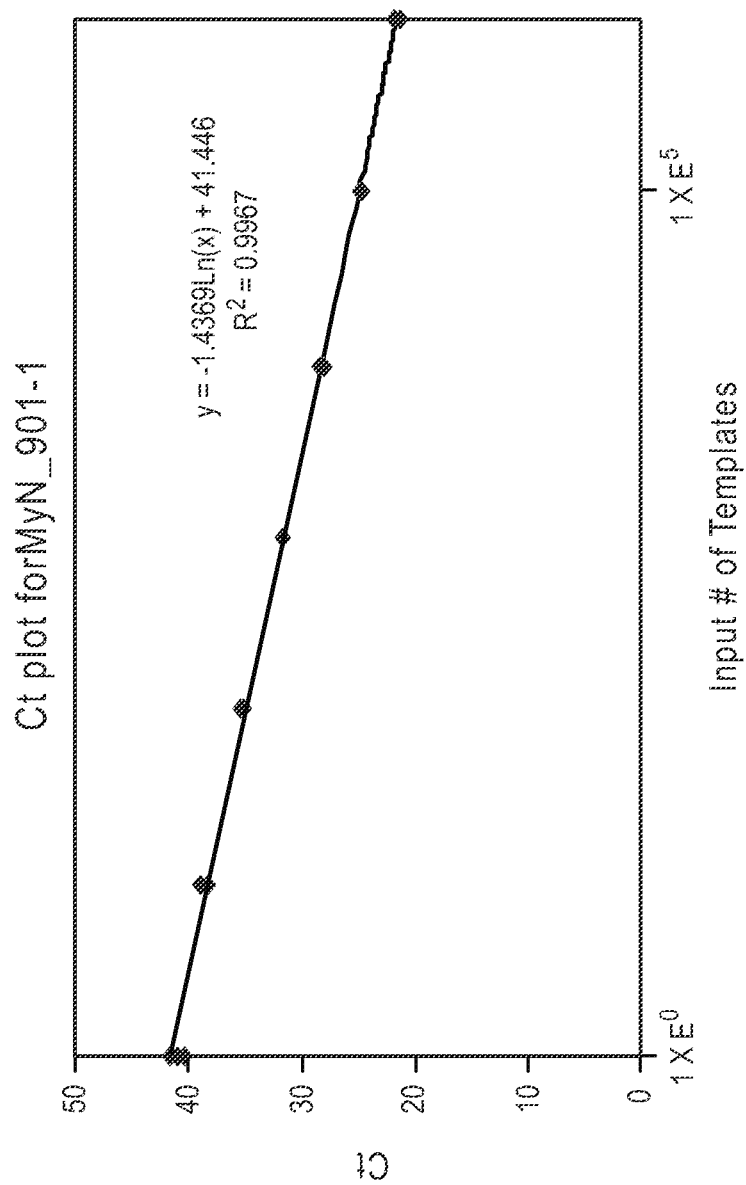
FIG. 3B is a Ct plot analysis of the data presented in FIG. 3A.

Results:

FIG. 3A illustrates the wide dynamic range of the PNA-based *Mycoplasma* real-time PCR assay. In this experiment, various amounts of *Mycoplasma pirum* genomic DNA were used as the template for the reaction. The amount of *M. pirum* genomic DNA used to generate each curve is given in nanograms, picograms or femptograms. Corresponding target copy numbers, calculated on the basis of both amount of DNA added and the genome size of *M. pirum*, are given in parentheses. This figure demonstrates that the assay performed well over a 6-log range of DNA target concentrations. FIG. 3B is a Ct plot for SEQ. ID. NO. 9. This plot illustrates the relationship between known concentrations of target DNA added to the reaction system and the resulting Ct value—the point at which the amplification curve crosses the detection threshold. This linear relationship can be used to calculate the concentration of target DNA initially present in unknown samples. Additionally, the slope of this line may be used to calculate the efficiency of the PCR reaction.

Figure 4:
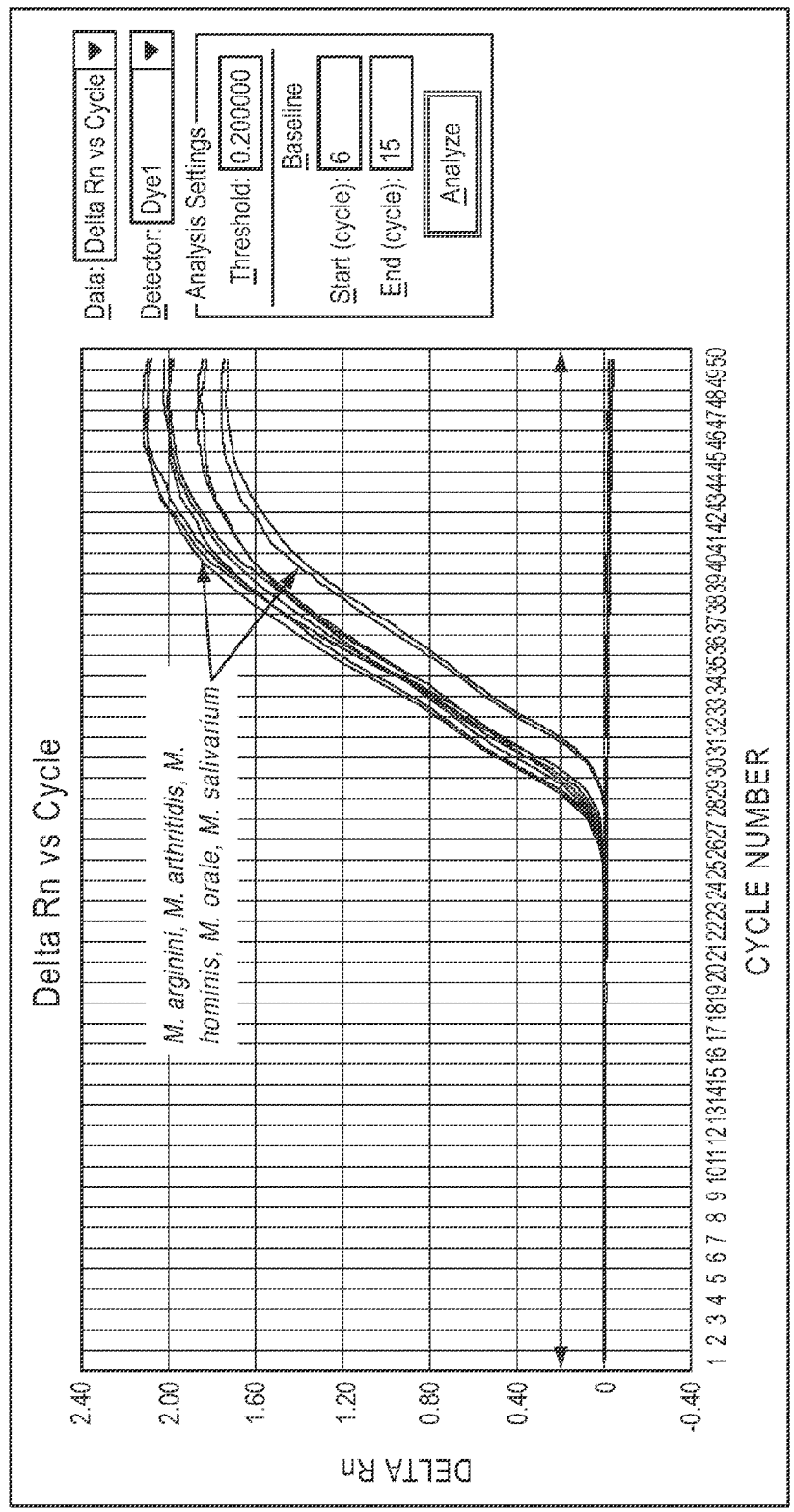
FIG. 4 is data output from an ABI 7700 for real-time sensitivity and specificity testing of an assay for Mollicutes using at least two nucleic acid primers and at least one PNA probe described herein.

FIG. 4 illustrates the specificity of the PNA probe corresponding to SEQ. ID. NO: 6 for it's expected target group (*Mycoplasma arginini, Mycoplasma arthriditis, Mycoplasma hominis, Mycoplasma orale, Mycoplasma salivarium* and related species). Non-target *Mycoplasma* species (*Mycoplasma fermentans, Acholeplasma laidlawii, Mycoplasma pirum, Mycoplasma pneumoniae*) did not generate a signal, despite the presence in the reaction of primers capable of producing an amplicon from the genomic DNA of these species.

Figure 5:
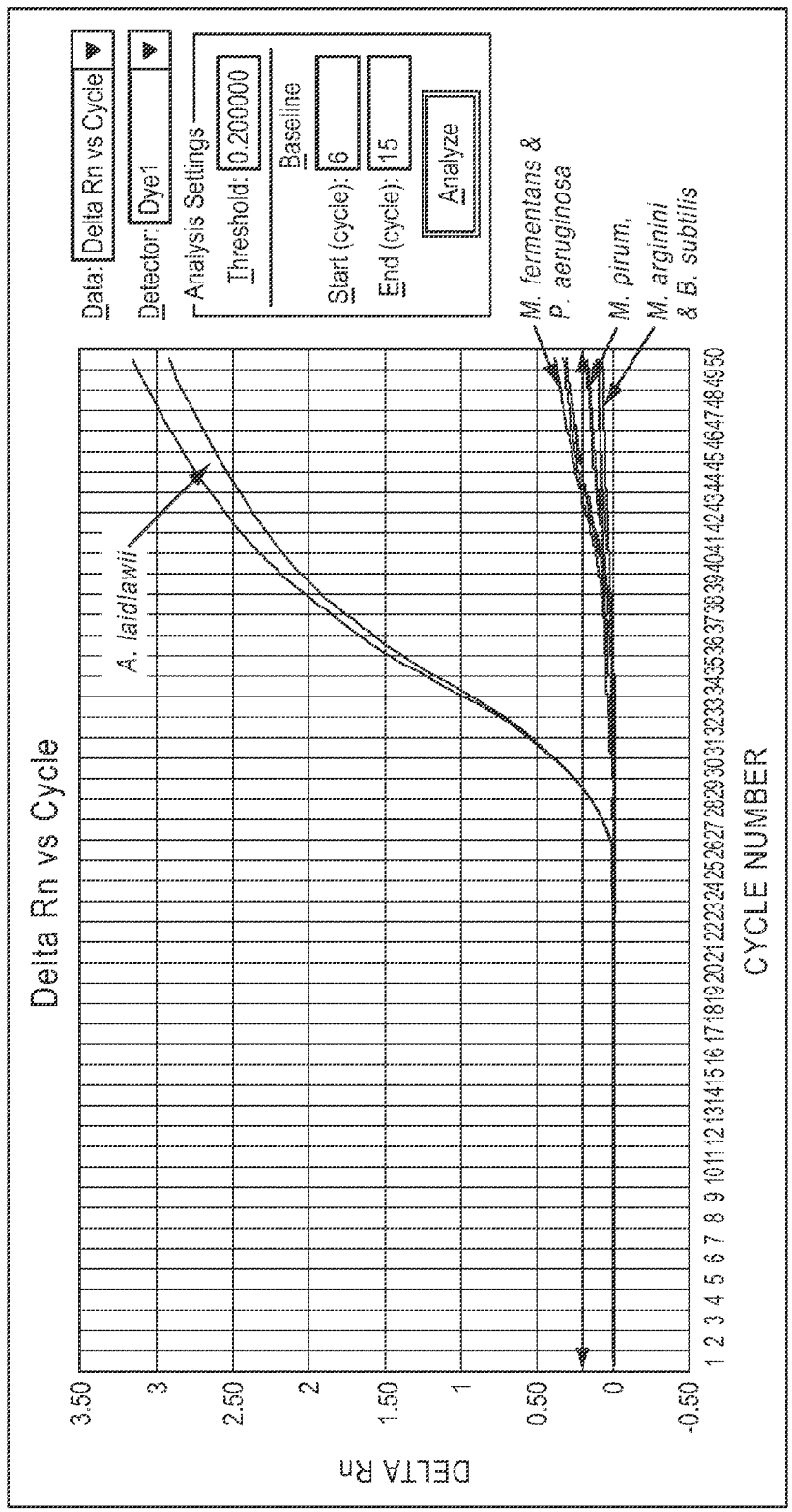
FIG. 5 is data output from an ABI 7700 for real-time sensitivity and specificity testing of an assay for Mollicutes using at least two nucleic acid primers and at least one PNA probe described herein.

FIG. 5 illustrates the specificity of the PNA probe corresponding to SEQ. ID. NO: 8 for it's expected target group (*Acholeplasma laidlawii*, and related species). Non-target *Mycoplasma* species (*Mycoplasma arginini, Mycoplasma fermentans, Mycoplasma pirum, Pseudomonas aeruginosa* and *Bacillus subtilis*) did not generate a signal, despite the presence in the reaction of primers capable of producing an amplicon from the genomic DNA of these species.

Figure 6:
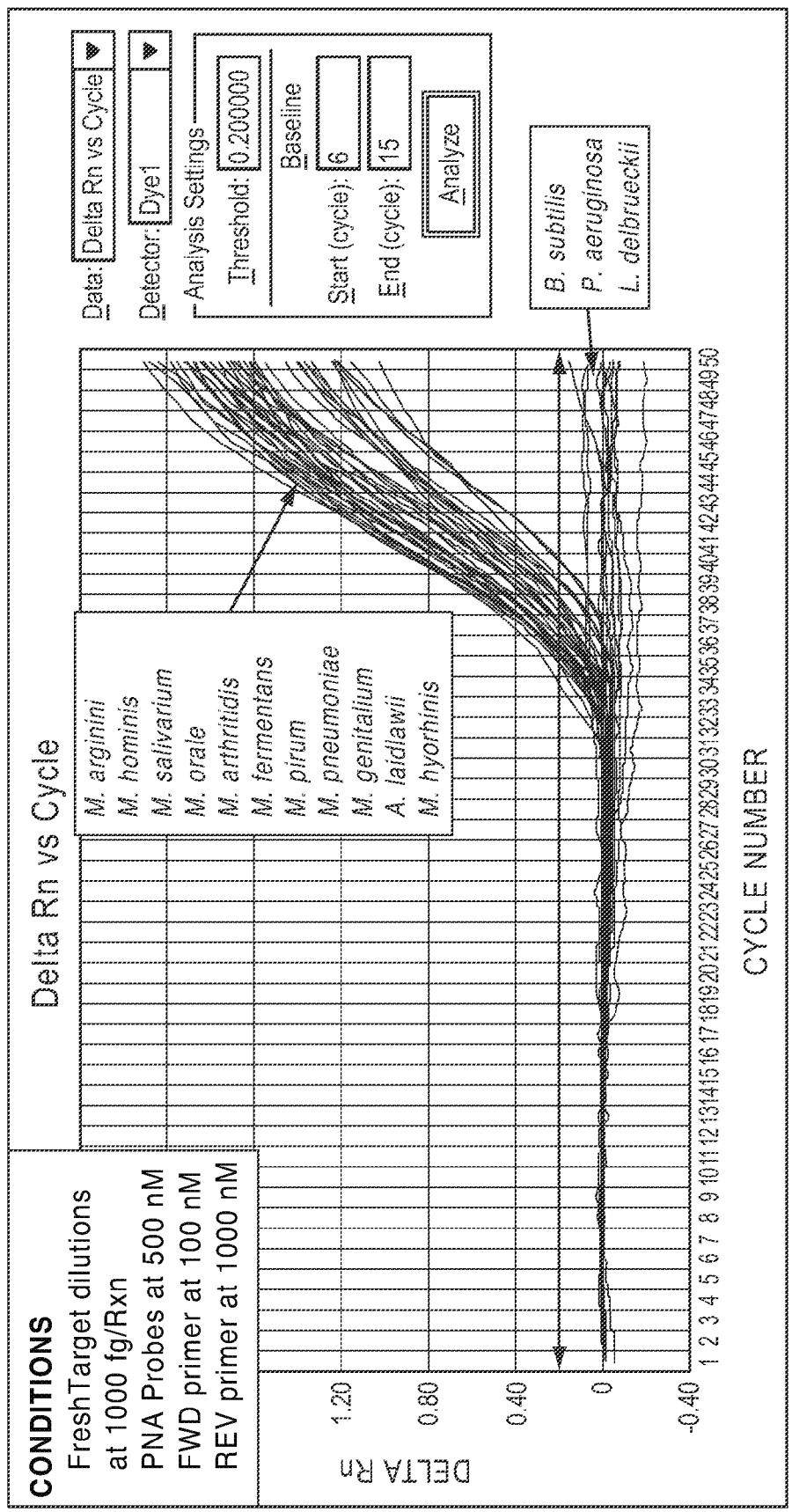
FIG. 6 is data output from an ABI 7700 for real-time sensitivity and specificity testing of an assay for Mollicutes using at least two nucleic acid primers and at least one PNA probe described herein.

FIG. 6 illustrates the selective identification of *Mycoplasma* species by the *Mycoplasma* real-time PCR assay. The multiplex assay containing DNA primers corresponding to SEQ. ID Nos. 1-5 and PNA probes corresponding to SEQ. ID. Nos. 6-9 were combined in a single tube with genomic DNA from both target and non-target bacteria. DNA from representatives of the four targeted groups of mycoplasmas and related Mollicutes was readily detected by this assay. DNA from representative non-target bacterial species (*Bacillus subtilis, Pseudomonas aeruginosa, Lactobacillus delbrueckii*) was not detected.

Figure 7:
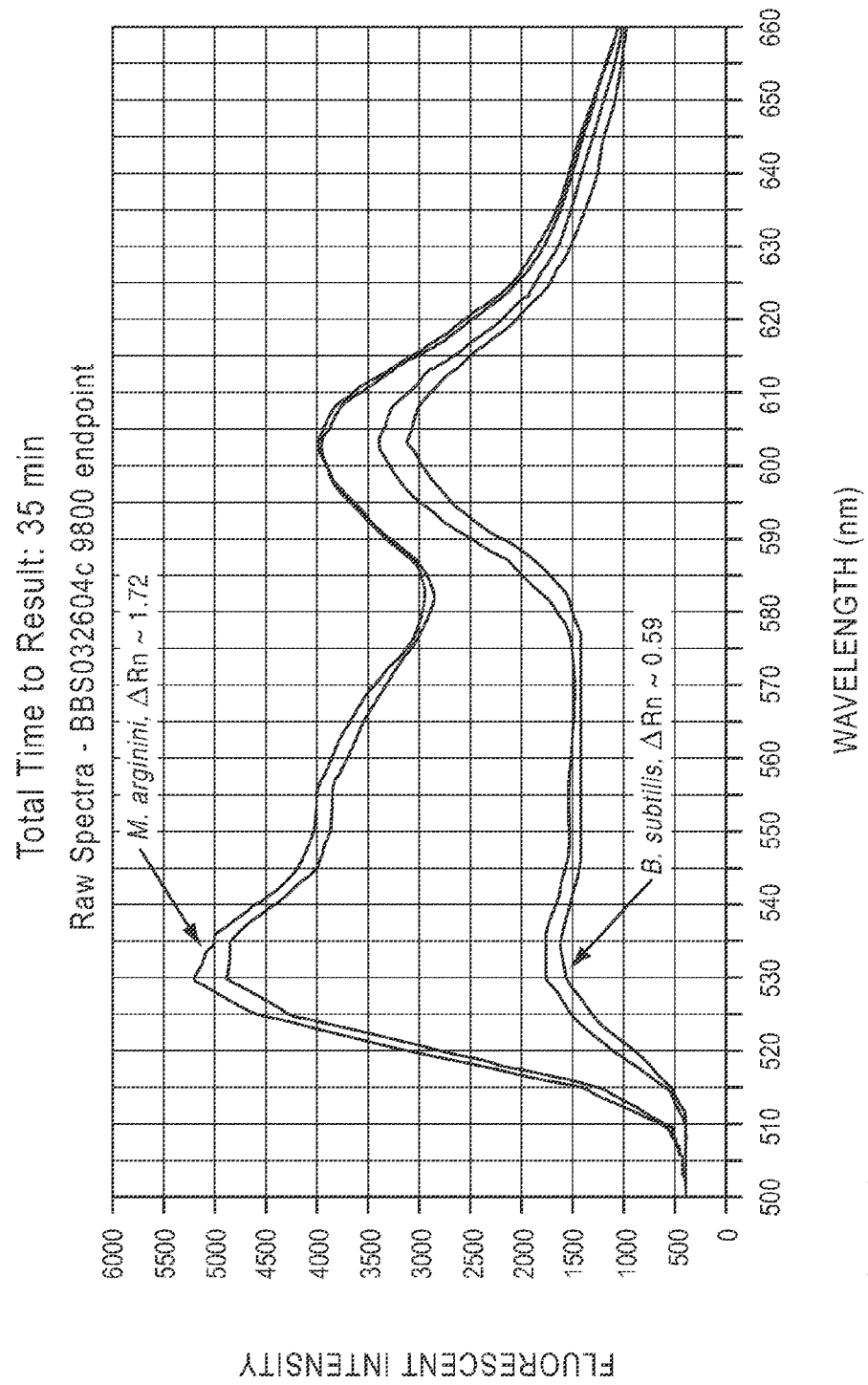
FIG. 7 is data output from an ABI 9800 pertaining to a rapid end-point assay for Mollicutes using nucleic acid primers and at least one PNA probe described herein.
Figure 8:
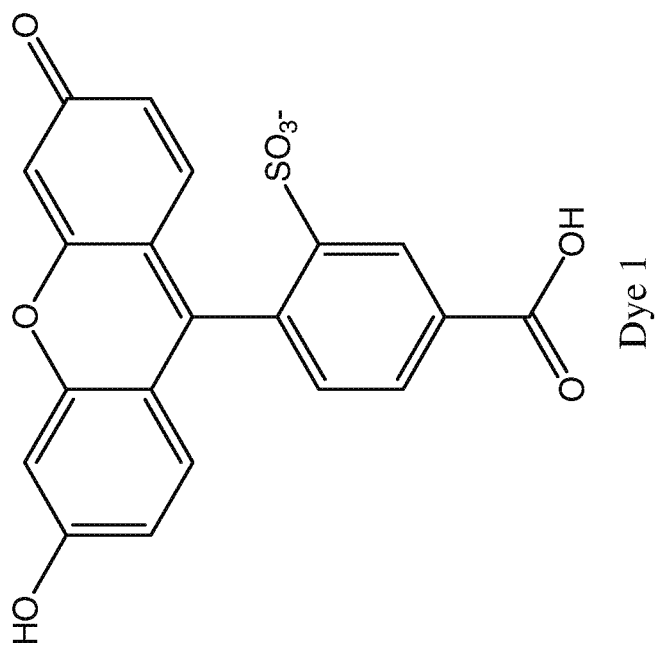
FIG. 8 is an illustration of the chemical structure of Dye 1.

FIG. 7 illustrates the utility of the DNA primers and PNA probes described here in conjunction with the Fast PCR System for rapid and selective endpoint detection of Mollicutes, in this case, *Mycoplasma arginini*. The large differential in final fluorescence values at 530 nm between the target organism (*Mycoplasma argnini*, delta Rn of ~1.72) and the non-target organism (*Bacillus subtilis*, delta Rn of ~0.59) highlights the specificity of the reaction. The secondary fluorescence maxima at ~605 nm belong to the internal standard and are not of diagnostic value.

Discussion:

Asymmetric PCR allows preferential amplification of one strand over another. This is accomplished by adding a larger amount of the primer that directs the synthesis of the strand that is desired in excess. The primer that is present in excess will consume a larger proportion of the limited resources available in the reaction tube (nucleotides, magnesium, etc.), leading to a bias in product formation, especially during the logarithmic phase of the reaction. In a PCR assay using the PNA-probes described in this example, the product that is desired in excess is the polynucleobase strand comprising the target sequence (i.e. the strand of the amplicon comprising a nucleobase sequence that is complementary to the PNA probe). In the assay described in this example, the forward primer (SEQ ID No. 1) was present at a level of 0.1 µM, while the reverse primers (SEQ ID Nos. 2-5) were present at a concentration of 1 µM each. PNA probes were used at a concentration of 0.5 µM.

Apart from their use in detecting *Mycoplasma* contamination in pharmaceutical materials or processes, the unique combination of primers and probes described in this example may also be useful for presence/absence detection of medically-relevant Mycoplasmas, as in silico specificity checks suggest they will be able to detect most of the *Mycoplasma* or *Ureaplasma* species associated with conditions such as non-gnococcal urethritis and other genitourinary infections in humans (Yoshida et al., 2002). These primers and probes may also be useful in veterinary diagnostic applications, as they are expected to detect *Mycoplasma* species implicated in economically important animal diseases (Persson et al., 2002).

The goal of this assay was to detect the largest number of species belonging to *Mycoplasma* and related genera of mollicutes. Given the size and phylogenetic diversity of the target group, it was not known prior to experimentation whether or not the selected primer sequences would have the operational specificities required by the assay. Therefore, it was somewhat surprising that although the target organisms *M. arginini* and *M. orale* show one mismatch to the reverse primer described by Sequence No. 2, these species could be readily detected under the final PCR conditions used. Similarly, *M. salivarium*, which shows two mismatches to this sequence, was also readily detected in the final assay.

While the present teachings are described in conjunction with various embodiments, it is not intended that the present teachings be limited to such embodiments. On the contrary, the present teachings encompass various alternatives, modifications and equivalents, as will be appreciated by those of skill in the art.

7. REFERENCES

1. Dussurget, O., and D. Roulland-Dussoix. 1994. Rapid, sensitive PCR-based detection of Mycoplasmas in simulated samples of animal sera. Appl. Environ. Microbiol. 60: 953-959.
2. Haier, J., M. Nasralla, A. R. Franco, and G. L. Nicolson. 1999. Detection of mycoplasmal infections in blood of patients with rheumatoid arthritis. Rheumatology 38: 504-509.
3. Hart, M. K., R. A. Del. Giudice, and G. W. Korch, Jr. 2002. Absence of *Mycoplasma* contamination in the anthrax vaccine. Emerg. Infect. Dis. 8: 94-96.
4. Jensen, J., Bruun, B., and B. Gahrn-Hansen. 1999. Unexpected cross-reaction with *Fusobacterium necrophorum* in a PCR for detection of Mycoplasmas. J. Clin. Microbiol. 37: 828-829.
5. Kidder, M., P. J. Chan, I. M. Seraj, W. C. Patton, and A. King. 1998. Assessment of archived paraffin-embedded cervical condyloma tissues for mycoplasma-conserved DNA using sensitive PCR-ELISA. Gynecol. Oncol. 71: 254-257.
6. Kong, F., James, G., Gordon, S. Zelynski, A., and G. L. Gilbert. 2001. Species-specific PCR for identification of common contaminant mollicutes in cell culture. Appl. Environ. Microbiol. 67: 3195-3200.
7. Persson, A., Jacobsson, K., Frykberg, L., Johansson, K.-E., and F. Poumarat. 2002. Variable surface protein Vmm of *Mycoplasma mycoides* subsp. *mycoides* small colony type. J. Bacteriol. 184: 3712-3722.
8. Razin, S., D. Yogev, and Y. Naot. 1998. Molecular biology and pathogenicity of Mycoplasmas. Microbiol. Mol. Biol. Rev. 62: 1094-1156.
9. Rottem, S, and M. F. Barile. 1993. Beware of mycoplasmas. Trends Biotechnol. 11: 143-151.
10. Tang, J., M. Hu, S. Lee, and R. Roblin. 2000. A polymerase chain reaction based method for detecting *Mycoplasma/Acholeplasma* contaminants in cell culture. J. Microbiol. Methods 39: 121-126.
11. Uphoff, C. C., and H. G. Drexler. 1999. Detection of *Mycoplasma* contaminations in cell cultures by PCR analysis. Hum. Cell 12: 229-236.

12. van Kuppeveld, F. J. M., J. T. M. van der Logt, A. F. Angulo, M. J. van Zoest, G. G. V. Quint, H. G. M. Niesters, J. M. D. Galama, and W. J. G. Melchers. 1992. Genus- and species-specific identification of mycoplasmas by 16S rRNA amplification. Appl. Environ. Microbiol. 58: 2606-2615.
13. van Kuppeveld, F. J. M., K.-E. Johansson, J. M. D. Galama, J. Kissing, G. Bölske, J. T. M. va der Logt, and W. J. G. Melchers. 1994. Detection of *Mycoplasma* contamination in cell cultures by a *Mycoplasma* group-specific PCR. Appl. Environ. Microbiol. 60: 149-152.
14. Yoshida, T., Maeda, S.-I., Deguchi, T., and H. Ishiko. 2002. Phylogeny-based rapid identification of mycoplasmas and ureaplasmas from urethritis patients. J. Clin. Microbiol. 40: 105-110.

---

We claim:

1. A mixture or kit comprising:
   a) five nucleic acid primers each having a length of 23-30 nucleotides, wherein each of the five primers comprise one of SEQ ID Nos.: 1-5, each of which primer hybridizes to a sequence within the nucleic acid of one or more Mollicutes; and
   b) four PNA probes, each of which probe comprises a probing nucleobase sequence of 12-20 nucleobase containing subunits, wherein the probing nucleobase sequence is selected from the group consisting of SEQ. ID. NO: 6, SEQ. ID. NO: 7, SEQ. ID. NO: 8, SEQ. ID. NO: 9, the complement to SEQ. ID. NO: 6, the complement to SEQ. ID. NO: 7, the complement to SEQ. ID. NO: 8 and the complement to SEQ. ID. NO: 9, and wherein each probe hybridizes to a target sequence within the nucleic acid of one or more Mollicutes.

2. The mixture or kit of claim 1, wherein the one or more Mollicutes are *Mycoplasma, Acholeplasma* or *Ureaplasma*.

3. The mixture or kit of claim 1, further comprising:
   c) other reagents selected to perform a PCR amplification reaction.

4. The mixture or kit of claim 1, further comprising an internal positive control.

5. The mixture or kit of claim 1, further comprising:
   c) other reagents selected to perform an in-situ hybridization assay.

6. The mixture or kit of claim 1, wherein the PNA probes are labeled with an energy transfer set.

7. The mixture or kit of claim 1, comprising:
   a) a primer of SEQ. ID. NO: 1; a primer of SEQ. ID. NO: 2; a primer of SEQ. ID. NO: 3; a primer of SEQ. ID. NO: 4; and a primer of SEQ. ID. NO: 5; and
   b) a PNA probe consisting of SEQ. ID. NO: 6 as a probing nucleobase sequence; a PNA probe consisting of SEQ.

ID. NO: 7 as a probing nucleobase sequence; a PNA probe consisting of SEQ. ID. NO: 8 as a probing nucleobase sequence; and PNA probe consisting of SEQ. ID. NO: 9 as a probing nucleobase sequence.

8. The mixture or kit of claim 1, comprising:
a) a primer of SEQ. ID. NO: 1; a primer of SEQ. ID. NO: 2; a primer of SEQ. ID. NO: 3; a primer of SEQ. ID. NO: 4; and a primer of SEQ. ID. NO: 5; and
b) a PNA probe consisting of the complement to SEQ. ID. NO: 6 as a probing nucleobase sequence; a PNA probe consisting of the complement to SEQ. ID. NO: 7 as a probing nucleobase sequence; a PNA probe consisting of the complement to SEQ. ID. NO: 8 as a probing nucleobase sequence; and a PNA probe consisting of the complement to SEQ. ID. NO: 9 as a probing nucleobase sequence.

9. The mixture or kit of claim 1, wherein mixture or kit further comprises blocking PNA probes.

10. The mixture or kit of claim 1, wherein at least one of the PNA probes is a blocking PNA probe.

* * * * *